(12) United States Patent
Ferreira et al.

(10) Patent No.: US 11,587,667 B2
(45) Date of Patent: Feb. 21, 2023

(54) CONTEXTUALLY ADAPTIVE DIGITAL PATHOLOGY INTERFACE

(71) Applicant: Ventana Medical Systems, Inc., Tucson, AZ (US)

(72) Inventors: Joao Ferreira, London (GB); Alexander Kalogrides, Tucson, AZ (US); Olivier Troy, Tucson, AZ (US); Eduardo Ferroao Ulrich, London (GB)

(73) Assignee: VENTANA MEDICAL SYSTEMS, INC., Tucson, AZ (US)

( * ) Notice: Subject to any disclaimer, the term of this patent is extended or adjusted under 35 U.S.C. 154(b) by 0 days.

(21) Appl. No.: 17/272,125

(22) PCT Filed: Aug. 26, 2019

(86) PCT No.: PCT/US2019/048060
§ 371 (c)(1),
(2) Date: Feb. 26, 2021

(87) PCT Pub. No.: WO2020/046773
PCT Pub. Date: Mar. 5, 2020

(65) Prior Publication Data
US 2021/0327564 A1 Oct. 21, 2021

Related U.S. Application Data

(60) Provisional application No. 62/726,081, filed on Aug. 31, 2018.

(51) Int. Cl.
G06F 3/0482 (2013.01)
G16H 30/40 (2018.01)
(Continued)

(52) U.S. Cl.
CPC .......... G16H 30/40 (2018.01); G06F 3/0482 (2013.01); G06F 3/04845 (2013.01);
(Continued)

(58) Field of Classification Search
None
See application file for complete search history.

(56) References Cited

U.S. PATENT DOCUMENTS 5,945,985 A * 8/1999 Babin ................. G09B 29/106
715/209
7,087,379 B2 8/2006 Light
(Continued)

FOREIGN PATENT DOCUMENTS

| JP | 2007-034824 A | 2/2007 |
| JP | 2016-511845 A | 4/2016 |

(Continued)

OTHER PUBLICATIONS

International Search Report received in International Patent Application No. PCT/US2019/048060, dated Nov. 25, 2019.
(Continued)

*Primary Examiner* — Rinna Yi
(74) *Attorney, Agent, or Firm* — Kilpatrick Townsend & Stockton LLP

(57) ABSTRACT

A method, system, and computer program product for an image visualization system (120) that includes a contextually adaptive digital pathology interface. At least one image of a biological sample stained for the presence of one or more biomarkers is obtained (300). The image is displayed on a display screen at a first zoom level (310), in which a first subset of user selectable elements are contemporaneously displayed (320). As a result of user input, the image being is displayed at a second zoom level (330), in which a second subset of user selectable elements are contemporaneously
(Continued)

displayed with the image (340). The one or more elements within the second subset of user selectable elements are disabled or hidden at the first zoom level, or one or more elements within the first subset of user selectable elements are disabled or hidden at the second zoom level.

21 Claims, 12 Drawing Sheets

(51) Int. Cl.
  *G16H 30/20* (2018.01)
  *G06F 3/04845* (2022.01)
(52) U.S. Cl.
  CPC ... *G16H 30/20* (2018.01); *G06F 2203/04803* (2013.01); *G06F 2203/04806* (2013.01)

(56) References Cited

U.S. PATENT DOCUMENTS

| | | |
|---|---|---|
| 2012/0320094 A1 | 12/2012 | Ruddle |
| 2014/0377753 A1 | 12/2014 | Bamford |
| 2015/0261422 A1* | 9/2015 | den Haring ........... G06F 3/0484 715/800 |
| 2015/0301732 A1 | 10/2015 | Henderson et al. |
| 2015/0347702 A1 | 12/2015 | Chukka |
| 2016/0216882 A1* | 7/2016 | Kiey .................... G16B 5/00 |
| 2017/0082627 A1 | 3/2017 | Dennis |
| 2017/0103521 A1 | 4/2017 | Chukka |
| 2017/0140246 A1 | 5/2017 | Barnes |
| 2017/0154420 A1* | 6/2017 | Barnes ................. G06T 5/003 |
| 2017/0243051 A1 | 8/2017 | Chukka |
| 2017/0323148 A1 | 11/2017 | Sarkar |
| 2017/0337251 A1* | 11/2017 | Kordasiewicz ....... G06F 16/285 |
| 2017/0337695 A1 | 11/2017 | Sarkar |
| 2017/0372117 A1 | 12/2017 | Bredno |
| 2021/0210194 A1* | 7/2021 | Hermans ............... G16H 30/20 |

FOREIGN PATENT DOCUMENTS

| | | |
|---|---|---|
| WO | WO2015/113895 | 8/2015 |
| WO | WO2016/120442 | 8/2016 |
| WO | 2017/197526 | 11/2017 |

OTHER PUBLICATIONS

Zamay et al., "Current and prospective protein biomarkers of lung cancer" Cancers. Nov. 2017; 9(11):155.
Application No. JP2021-510327, Office Action, dated Nov. 2, 2022, 6 pages (pp. 1-3 English translation, pp. 4-6 original document).

\* cited by examiner

CONTEXTUALLY ADAPTIVE DIGITAL PATHOLOGY INTERFACE

CROSS-REFERENCE TO RELATED APPLICATIONS

This application claims the benefit of U.S. Patent Provisional Application No. 62/726,081, filed Aug. 31, 2018, which is incorporated herein by reference in its entirety for all purposes.

BACKGROUND OF THE DISCLOSURE

Digital pathology refers to the management and interpretation of pathology information in a digital environment. Scanning devices are used to image slides of biological samples, which may be stained, such that digital slides, e.g., whole slide images, are generated. Digital pathology software enables digital slides to be stored in a computer memory device, viewed on a computer monitor, and analyzed for pathology information.

BRIEF SUMMARY OF THE DISCLOSURE

The present disclosure provides a graphical user interface adapted to provide visualizations of images of biological samples stained for the presence of one or more biomarkers, and to enable the display of contextually relevant elements (e.g. analysis tools, viewer panels) to a user based on whether pre-established criteria are met. In some embodiments, contextually relevant elements are provided to the user based on a selected zoom level or a selection of an image having a particular stain. It is believed that by providing only those elements that are contextually relevant, the user is not overwhelmed with visualized elements (e.g. those that are not appropriate or those that would be ineffective in a given context) and can instead select the correct elements based on a condition state (e.g. a selected zoom level, a selected image type, a selected tissue type, a selection of a whole slide image versus a slide derived from a tissue microarray, a selected slide having a particular stain applied (for instance, H&E), a selected slide stained for the presence of a particular biomarker, a selected slide stained using immunohistochemistry as opposed to in situ hybridization, a selected slide that has had certain image analysis algorithms applied). It is further believed that providing only elements that are contextually relevant allows for a quicker and more accurate review of presented image data. In addition, given that display screens have a limited size and resolution, it is often difficult to provide multiple visualizations at once or if multiple visualizations are provided, they may overlap or obstruct a user's view of important elements. By displaying only those elements that are contextually relevant given a particular condition (e.g. a particular zoom level selected by a user), the most appropriate elements may be prioritized and visualized taking into account the limited display size and resolution.

In some embodiments, a computing device comprises a display screen, the computing device configured to: access at least one image of a biological sample stained for the presence of one or more biomarkers (e.g. HER2, PD-L1, etc.) from one or more memories communicatively coupled to the computing device; display on the display screen a first visualization of the at least one image at a first zoom level, and contemporaneously with displaying the first visualization, display on the display screen a first subset of user selectable elements; and subsequently display on the display screen a second visualization of the at least one image at a second zoom level, wherein the second zoom level is greater than the first zoom level, and contemporaneously with displaying the second visualization, display on the display screen a second subset of user selectable elements, (i) one or more elements within the second subset of user selectable elements are disabled or hidden at the first zoom level, or (ii) one or more elements within the first subset of user selectable elements are disabled or hidden at the second zoom level.

In some embodiments, the second zoom level at least meets a pre-determined threshold zoom value. In some embodiments, the second subset of user selectable elements are contextually relevant at the second zoom level. In some embodiments, the user selectable elements comprise menu bar tools and contextual menu items. By way of example, the tools and menus are contextual. When a user is fully "zoomed out," only the relevant tools to use in that context are enabled (see FIG. 4A). When the user zooms in to a specified zoom level (see FIG. 4B), tools in the tool bar become enabled and/or contextual panels appear. The user can now use these tools when in the "zoomed in" context of the slide. As such, the tools available in either a first series of tools or in a second series of tools depends on the zoom level selected by a user, e.g. a second zoom level compared to a first zoom level, wherein the second zoom level meets or exceeds a pre-determined threshold zoom level for enabling the second series of tools.

In some embodiments, the menu bar tools comprise image annotation tools, slide setup tools, slide selection tools, navigation tools and viewing tools. In some embodiments, the image annotation tools are enabled at the second zoom level. In some embodiments, the image annotation tools are hidden at the first zoom level. In some embodiments, the image annotation tools comprise region of interest identification tools, measurement tools, indicia drawing tools, and region exclusion tools.

In some embodiments, the computing device is further configured to display on the display screen one or more viewer panels at the second zoom level, wherein the one or more viewer panels for display at the second zoom level are disabled at the first zoom level. In some embodiments, the first zoom level is a 1× zoom level (i.e. the lowest zoom level, such as an image scanned or otherwise captured at no magnification) and wherein the first visualization comprises at least one representation including the at least one image of the biological sample. In some embodiments, the at least one representation further comprises a portion comprising identifying indicia.

In some embodiments, a computing device comprises a display screen, the computing device configured to: access at least one image of a biological sample stained for the presence of one or more biomarkers from one or more memories communicatively coupled to the computing device; display on the display screen at least a first representation comprising the at least one image at a first zoom level, and contemporaneously with displaying the first representation, display on the display screen at least a first viewer panel; subsequently display on the display screen a second representation of the at least one image at a second zoom level, wherein the second zoom level is greater than the first zoom level, and contemporaneously with displaying the second representation, display on the display screen at least a second viewer panel in addition to the first viewer panel, wherein the at least the second viewer panel is hidden from display at the first zoom level.

In some embodiments, a third viewer panel is displayed on the display screen contemporaneously with the displaying of the second display panel, wherein the third viewer panel is hidden from display at the first zoom level. In some embodiments, menu bar icons are enabled on the display screen contemporaneously with the displaying of the second display panel. In some embodiments, the menu bar icons displayed are selected from the group consisting of region of interest identification tools, measurement tools, indicia drawing tools, and region exclusion tools. In some embodiments, the at least the first representation comprises: (i) a first portion comprising the at least one image of the biological sample at the first zoom level, and (ii) a second portion comprising identifying indicia. In some embodiments, the identifying indicia comprises an identification of a biomarker.

In some embodiments, a method comprises: displaying, on a computing device having a display screen, a first visualization comprising at least one image of a stained biological sample, wherein the first visualization is displayed in a first condition state, and contemporaneously with displaying the first visualization, display on the display screen at least one of a first viewer panel or a first series of user selectable elements; and subsequently display on the display screen a second visualization of the at least one image in a second condition state, wherein the second condition state is derived as a result of a user selection, and contemporaneously with displaying the second visualization, display on the display screen at least one of a second series of user selectable elements that are not enabled in the first condition state or a second viewer panel in addition to the first viewer panel, wherein the second viewer panel is hidden from display at the first zoom level. In some embodiments, the first condition state is a default state. In some embodiments, the user selection is a zoom level, and wherein the second condition is a zoom level greater than the default zoom level, in some embodiments, the user selection is an image selection, wherein the image selected for the second condition comprises a different stain than an image of the first condition state.

In some embodiments, a method comprises: displaying, on a computing device having a display screen, a first visualization comprising at least one image of a stained biological sample, wherein the first visualization is displayed at a first zoom level, and contemporaneously with displaying the first visualization, display on the display screen at least one of a first viewer panel or a first series of user selectable elements; and subsequently display on the display screen a second visualization of the at least one image in at a second zoom level, wherein the second zoom level is greater than the first zoom level, and contemporaneously with displaying the second visualization, display on the display screen at least one of a second series of user selectable elements that are hidden or not enabled at the first zoom level or at least a second viewer panel in addition to the first viewer panel, wherein the second viewer panel is hidden from display at the first zoom level.

In some embodiments, the first zoom level is a default zoom level. In some embodiments, the second zoom level is one which sufficiently resolves a cluster of cells or which sufficiently resolves cell nuclei. In some embodiments, the first zoom level is a lowest available zoom level and the second zoom level is at least 5×. In some embodiments, the first zoom level is a lowest available zoom level and the second zoom level is at least 10×.

In some embodiments, the second subset of user selectable elements are contextually relevant at the second zoom level. In some embodiments, the user selectable elements comprise menu bar tools and contextual menu items. In some embodiments, the menu bar tools comprise image annotation tools, slide setup tools, slide selection tools, navigation tools and viewing tools. In some embodiments, the image annotation tools are enabled at the second zoom level. In some embodiments, the image annotation tools are hidden at the first zoom level. In some embodiments, the image annotation tools comprise region of interest identification tools, measurement tools, indicia drawing tools, and region exclusion tools.

In some embodiments, the first visualization includes at least one representation comprising: (i) a first portion comprising the at least one image of the biological sample at the first zoom level, and (ii) a second portion comprising identifying indicia. In some embodiments, the identifying indicia comprises an identification of a biomarker.

In some embodiments, a non-transitory computer-readable medium stores instructions which, when executed by one or more processors of a computing system, causes the computing system to display on the display screen a first visualization of the at least one image at a first zoom level, and contemporaneously with displaying the first representation, display on the display screen a first subset of user selectable tools; and subsequently display on the display screen a second visualization of the at least one image at a second zoom level, wherein the second zoom level is greater than the first zoom level, and contemporaneously with displaying the second representation, display on the display screen a second subset of user selectable tools, wherein one or more tools within the second subset of user selectable tools are not enabled at the first zoom level.

BRIEF DESCRIPTION OF THE FIGURES

For a general understanding of the features of the disclosure, reference is made to the drawings. In the drawings, like reference numerals have been used throughout to identify identical elements.

The patent or application file contains at least one drawing executed in color. Copies of this patent or patent application publication with color drawings will be provided to the Office upon request and the payment of the necessary fee.

DETAILED DESCRIPTION

Figure 1:
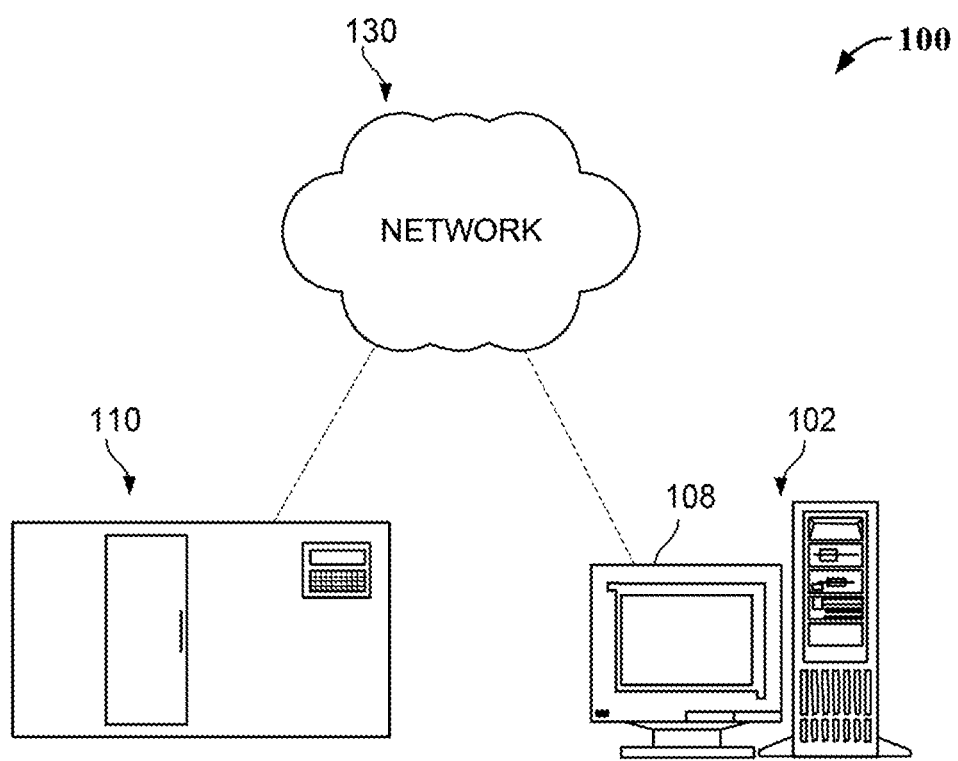
FIG. 1 illustrates a system including a computer having one or more processors and a scanning device, where the computer and the scanning device are communicatively coupled, such as through a network, in accordance with some embodiments.

It should also be understood that, unless clearly indicated to the contrary, in any methods claimed herein that include more than one step or act, the order of the steps or acts of the method is not necessarily limited to the order in which the steps or acts of the method are recited.

As used herein, the singular terms "a," "an," and "the" include plural referents unless context clearly indicates otherwise. Similarly, the word "or" is intended to include "and" unless the context clearly indicates otherwise. The term "includes" is defined inclusively, such that "includes A or B" means including A, B, or A and B.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of" or "exactly one of" "Consisting essentially of," when used in the claims, shall have its ordinary meaning as used in the field of patent law.

The terms "comprising," "including," "having," and the like are used interchangeably and have the same meaning. Similarly, "comprises," "includes," "has," and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c. Similarly, the phrase: "a method involving steps a, b, and c" means that the method includes at least steps a, b, and c. Moreover, while the steps and processes may be outlined herein in a particular order, the skilled artisan will recognize that the ordering steps and processes may vary.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in some embodiments, to at least one, optionally including more than one, A, with no B present (and optionally including elements other than B); in some embodiments, to at least one, optionally including more than one, B, with no A present (and optionally including elements other than A); in yet another embodiment, to at least one, optionally including more than one, A, and at least one, optionally including more than one, B (and optionally including other elements); etc.

As used herein, the term "image data" encompasses raw image data acquired from the biological tissue sample, such as by means of an optical sensor or sensor array, or pre-processed image data. In particular, the image data may comprise a pixel matrix.

As used herein, the terms "image," "image scan," or "scanned image" encompasses raw image data acquired from the biological tissue sample, such as by means of an optical sensor or sensor array, or pre-processed image data. In particular, the image data may comprise a pixel matrix.

As used herein, the term "biological sample," "tissue sample," "specimen" or the like refers to any sample including a biomolecule (such as a protein, a peptide, a nucleic acid, a lipid, a carbohydrate, or a combination thereof) that is obtained from any organism including viruses. Other examples of organisms include mammals (such as humans; veterinary animals like cats, dogs, horses, cattle, and swine; and laboratory animals like mice, rats and primates), insects, annelids, arachnids, marsupials, reptiles, amphibians, bacteria, and fungi. Biological samples include tissue samples (such as tissue sections and needle biopsies of tissue), cell samples (such as cytological smears such as Pap smears or blood smears or samples of cells obtained by microdissection), or cell fractions, fragments or organelles (such as obtained by lysing cells and separating their components by centrifugation or otherwise). Other examples of biological samples include blood, serum, urine, semen, fecal matter, cerebrospinal fluid, interstitial fluid, mucous, tears, sweat, pus, biopsied tissue (for example, obtained by a surgical biopsy or a needle biopsy), nipple aspirates, cerumen, milk, vaginal fluid, saliva, swabs (such as buccal swabs), or any material containing biomolecules that is derived from a first biological sample. In certain some embodiments, the term "biological sample" as used herein refers to a sample (such as a homogenized or liquefied sample) prepared from a tumor or a portion thereof obtained from a subject.

As used herein, the term "slide" refers to any substrate (e.g., substrates made, in whole or in part, glass, quartz, plastic, silicon, etc.) of any suitable dimensions on which a biological specimen is placed for analysis, and more particularly to a "microscope slide" such as a standard 3 inch by 1-inch microscope slide or a standard 75 mm by 25 mm microscope slide. Examples of biological specimens that can be placed on a slide include, without limitation, a cytological smear, a thin tissue section (such as from a biopsy), and an array of biological specimens, for example a tissue array, a cellular array, a DNA array, an RNA array, a protein array, or any combination thereof. Thus, in some embodiments, tissue sections, DNA samples, RNA samples, and/or proteins are placed on a slide at particular locations. In some embodiments, the term slide may refer to SELDI and MALDI chips, and silicon wafers.

As used herein, the terms "stain," "staining," or the like as used herein generally refers to any treatment of a biological specimen that detects and/or differentiates the presence, location, and/or amount (such as concentration) of a particular molecule (such as a lipid, protein or nucleic acid) or particular structure (such as a normal or malignant cell, cytosol, nucleus, Golgi apparatus, or cytoskeleton) in the biological specimen. For example, staining can provide contrast between a particular molecule or a particular cellular structure and surrounding portions of a biological specimen, and the intensity of the staining can provide a measure of the amount of a particular molecule in the specimen. Staining can be used to aid in the viewing of molecules, cellular structures and organisms not only with bright-field microscopes, but also with other viewing tools, such as phase contrast microscopes, electron microscopes, and fluorescence microscopes. Some staining performed by the system can be used to visualize an outline of a cell. Other staining performed by the system may rely on certain cell components (such as molecules or structures) being stained without or with relatively little staining other cell components. Examples of types of staining methods performed by the system include, without limitation, histochemical methods, immunohistochemical methods, and other methods based on reactions between molecules (including non-covalent binding interactions), such as hybridization reactions between nucleic acid molecules. Particular staining methods include, but are not limited to, primary staining methods (e.g., H&E staining, Pap staining, etc.), enzyme-linked immunohistochemical methods, and in situ RNA and DNA hybridization methods, such as fluorescence in situ hybridization (FISH).

As used herein, the term "user interface" refers to the interface that allows the user, for example end users such as histologists and/or pathologists, to input commands and data and receive results, such as a graphical user interface (GUI). The terms "user interface" and "graphical user interface" are used interchangeably herein.

As described in further detail herein, the present disclosure is directed to a graphical user interface which allows a user to view and/or analyze one or more images of biological samples stained for the presence of one or more biomarkers, whereby the visualization of certain elements and/or the availability of certain analysis and/or processing tools are provided to the user on a contextual basis. In some embodiments, the graphical user interface is adapted to provide contextually relevant visualizations and elements for selection based on whether a pre-established condition has been met. In some embodiments, the pre-established condition is a selection made by a user. For example, a selection may be a zoom level, or a magnification level selected by a user, where different zoom level or magnification level selections cause the graphical user interface to adaptively generate certain visualizations or to enable certain user configurable items, e.g. annotation tools, image processing tools, etc. In some embodiments, the graphical user interface adjusts those visualizations, analysis tools and/or viewer panels which are provided to the user (such as for display on a display) depending on a selected zoom level, e.g. a first subset of contextually relevant tools may be presented to the user at a lowest zoom level (e.g. no optical magnification as compared with, for example, a 10×, 20×, or 40× optical magnification), while a more inclusive second subset of tools may be presented to the user at a greater zoom level of 10× where the additional tools included within the second subset are again contextually relevant for the 10× zoom level. By way of another example, a selection may be a particular type of tissue (i.e. an image of a tissue) selected by the user or an image of a tissue sample stained for the presence of a particular biomarker.

It is believed that by presenting only those visualizations, analysis tools, viewer panels, etc. that are contextually relevant to a pre-established condition, e.g. at a selected zoom level, a selected tissue type, a selected slide having a particular stain applied, a selected slide stained for the presence of a particular biomarker, a selection of a whole slide image as opposed to a tissue microarray, etc., a user may be able to interact more efficiently with the software. Said another way, since the user is not overwhelmed with the availability of a multitude tools and/or viewer panels that are not relevant at a particular zoom level, the operator may be able to interact more efficiently with the graphical user interface, ultimately resulting in a quicker review and analysis of the images of the tissue samples presented.

In some embodiments, systems of the present disclosure are adapted to facilitate the interpretation and reporting of image data obtained from a subject (e.g. a human patient). In some embodiments, image data is acquired from a scanning device (such as the VENTANA DP 200 scanner, available from Ventana Medical Systems, Inc., Tucson, Ariz.) and the image data may be stored in a database, such as a networked database, for later visualization and analysis. For example, image data may be acquired using a scanning device and the scanned image data stored in a file located on a storage subsystem 104 or a networked server, whereby the file may be later retrieved for visualization and analysis (see FIG. 1). In some embodiments, software, such as an image visualization and analysis application, is run directly on a system and the image data is retrieved from the networked server for interpretation and reporting by a user interacting with the software (see FIG. 2A). In some embodiments, software, such as an image visualization and analysis application, is run on a remote system and a client interface or client portal is used to access the system, and whereby image data may be retried from a storage subsystem for visualization and analysis (see FIG. 2B).

The systems and methods provided herein can be applied to the visualization and analysis of any type of image of a tissue stained for the presence of one or more biomarkers. For example, the biological sample may be stained through application of one or more stains, and the resulting image or image data comprises signals corresponding to each of the one or more stains. In some embodiments, the input images are simplex images having only a single stain (e.g., stained with 3,3'-diaminobenzidine (DAB)). In some embodiments, the biological sample may be stained in a multiplex assay for two or more stains (thus providing multiplex images). In some embodiments, the biological samples are stained for at least two biomarkers. In some embodiments, the biological samples are stained for the presence of at least two biomarkers and also stained with a primary stain (e.g. hematoxylin). In some embodiments, the biological samples are stained for the presence of at least one protein biomarker and at least two nucleic acid biomarkers (e.g. DNA, RNA, microRNAs, etc.).

In some embodiments, the biological samples are stained in an immunohistochemistry assay for the presence of one or more protein biomarkers. For example, the biological sample may be stained for the presence of a human epidermal growth factor receptor 2 protein (HER2 protein). Currently in the United States, there are two Food and Drug Administration (FDA) approved methods for HER2 assessment: HerceptTest™ (DAKO, Glostrup Denmark) and HER2/neu (4B5) rabbit monoclonal primary antibody (Ventana, Tucson, Ariz.).

In some embodiments, the biological sample is stained for the presence of estrogen receptor (ER), progesterone receptor (PR), or Ki-67. In yet other embodiments, the biological sample is stained for the presence of EGFR or HER3. Examples of other protein biomarkers are described by Zamay et. Al., "Current and Prospective Biomarkers of Long Cancer," Cancers (Basel), 2018 November; 9(11), the disclosure of which is hereby incorporated by reference herein in its entirety. Examples of protein biomarkers described by Zamay include CEACAM, CYFRA21-1, PKLK, VEGF, BRAF, and SCC.

In some embodiments, the biological samples are stained in an in situ hybridization (ISH) assay for the presence of one or more nucleic acids, including mRNA. U.S. Pat. No. 7,087,379 (the disclosure of which is hereby incorporated by reference herein in its entirety) describes methods of staining samples with ISH probes such that individual spots (or dots), representing single gene copies, may be observed and detected. In some embodiments, several target genes are simultaneously analyzed by exposing a cell or tissue sample to a plurality of nucleic acid probes that have been labeled with a plurality of different nucleic acid tags.

FIG. 1 sets forth a system 100 (a computer or computing device) including an scanning device 110 communicatively coupled to a processing subsystem 102. The scanning device 110 can be coupled to the processing subsystem 102 either directly (e.g., through one or more communication cables) or through one or more wired and/or wireless networks 130. In some embodiments, the processing subsystem 102 may be included in or integrated with the scanning device 110. In some embodiments, the system 100 may include software to command the scanning device 110 to perform certain operations using certain user configurable parameters, and to send resulting imaging data acquired to the processing subsystem 102 or a storage subsystem (e.g. a local storage subsystem or a networked storage device). In some embodiments, either the processing subsystem 102 or the scanning device 110 may be coupled to a network 130. In some embodiments, a storage device is coupled to the network 130 for storage or retrieval of image data, subject information, and/or other tissue data. The processing subsystem 102 may include a display 108 and one or more input devices (not illustrated) for receiving commands from a user or operator (e.g. a technician, histologist, or pathologist).

In some embodiments, a user interface is rendered by processing subsystem 102 and is provided on display 108 to (i) facilitate the analysis, interpretation, and/or reporting of imaging data and/or subject data; (ii) to retrieve data from a scanning device; or (iii) to retrieve imaging data, subject information, or other clinical information from a database, such as one available through a network. In some embodiments, the network 130 enables access to a processing subsystem 102 and/or a scanning device 110 remotely, such as through a client interface or client portal (not illustrated). In this way, a remote user may access the processing subsystem 102 such that image visualization and analysis software may be run remotely on the processing subsystem 102. In some embodiments, the client interface or client portal may also enable the retrieval of stored reports after analysis of the imaging data.

Figure 2A:
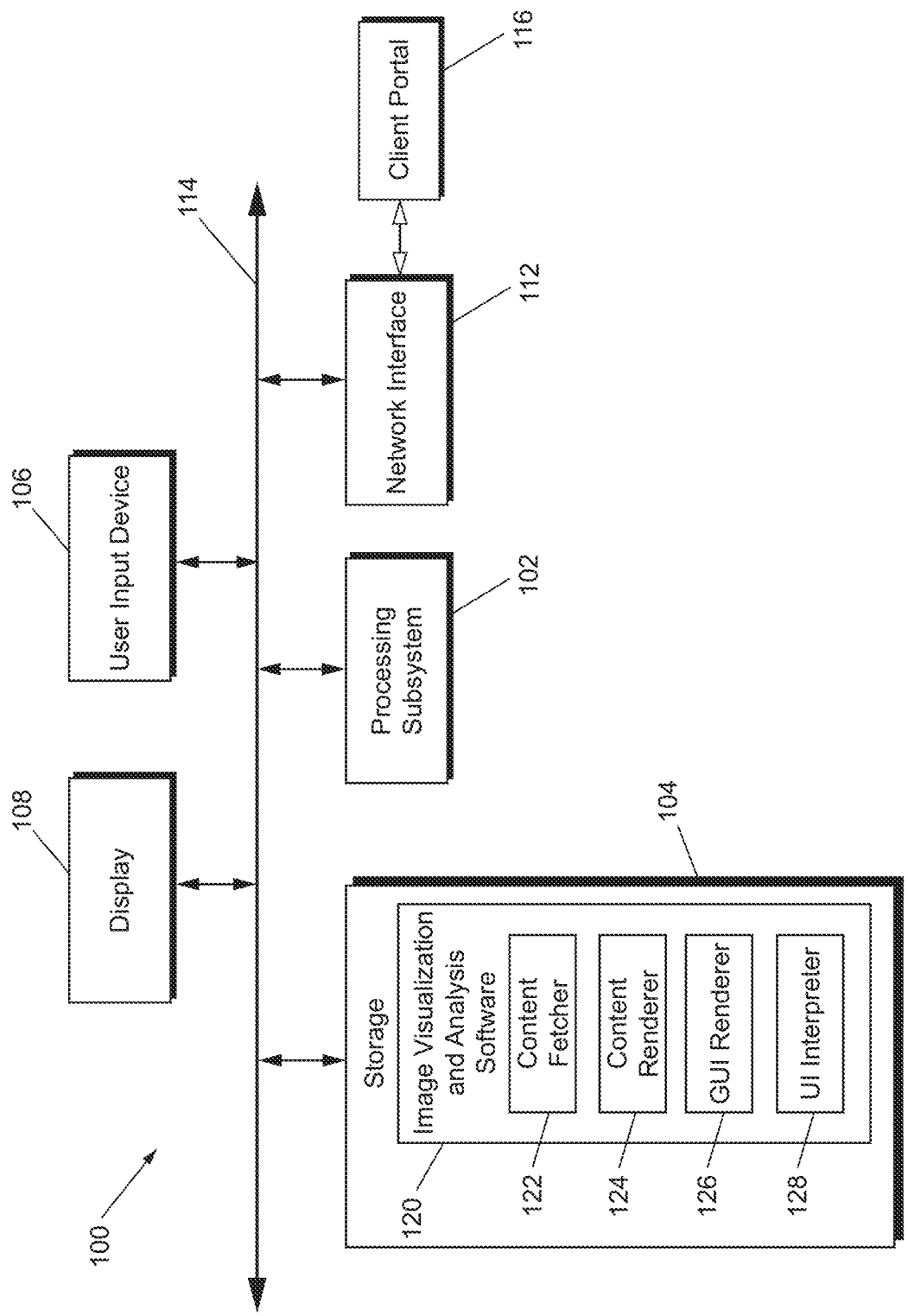
FIG. 2A illustrates a system including a processing subsystem, a storage subsystem, an output device, and an input device, each of the components communicatively coupled through a bus, a network, or other wired or wireless interconnect, in accordance with some embodiments. The system may also include software to enable remote access, i.e. a client portal or client interface.

FIG. 2A is a block diagram of a system 100 according to an embodiment of the present disclosure. System 100 can be implemented using any type of user-operable computing device, including desktop computers, laptop computers, tablet computers, handheld devices (e.g., smart phones, media players), and so on. System 100 can include a number of interconnected components such as processing subsystem 102, storage subsystem 104, user input device 106, display 108, and network interface 112 communicating via bus 114, as discussed in more detail below. In some embodiments, the system 100 depicted in FIG. 2A may be accessed remotely, e.g. one or more remote users may access system 100, such as over a network, such that image data stored within storage subsystem 104 may be reviewed, interpreted, analyzed, and/or reported.

Processing subsystem 102 can include a single processor, which can have one or more cores, or multiple processors, each having one or more cores. In some embodiments, processing subsystem 102 can include one or more general-purpose processors (e.g., CPUs), special-purpose processors such as graphics processors (GPUs), digital signal processors, or any combination of these and other types of processors. In some embodiments, some or all processors in processing subsystem can be implemented using customized circuits, such as application specific integrated circuits (ASICs) or field programmable gate arrays (FPGAs). In some embodiments, such integrated circuits execute instructions that are stored on the circuit itself. In some embodiments, processing subsystem 102 can retrieve and execute instructions stored in storage subsystem 104, and the instructions may be executed by processing subsystem 102 regardless of whether a user accesses the system locally or remotely, such as through client portal 116. By way of example, processing subsystem 102 can execute instructions to receive and process image data stored within a local or networked storage system and display the image data (e.g. display a whole slide scanned image, or a magnified portion of any whole slide scanned image).

Storage subsystem 104 can include various memory units such as a system memory, a read-only memory (ROM), and a permanent storage device. A ROM can store static data and instructions that are needed by processing subsystem 102 and other modules of system 100. The permanent storage device can be a read-and-write memory device. This permanent storage device can be a non-volatile memory unit that stores instructions and data even when system 100 is powered down. In some embodiments, a mass-storage device (such as a magnetic or optical disk or flash memory) can be used as a permanent storage device. Other embodiments can use a removable storage device (e.g., a flash drive) as a permanent storage device. The system memory can be a read-and-write memory device or a volatile read-and-write memory, such as dynamic random access memory. The system memory can store some or all of the instructions and data that the processor needs at runtime.

Storage subsystem 104 can include any combination of non-transitory computer readable storage media including semiconductor memory chips of various types (DRAM, SRAM, SDRAM, flash memory, programmable read-only memory) and so on. Magnetic and/or optical disks can also be used. In some embodiments, storage subsystem 104 can include removable storage media that can be readable and/or writeable; examples of such media include compact disc (CD), read-only digital versatile disc (e.g., DVD-ROM, dual-layer DVD-ROM), read-only and recordable Blu-ray® disks, ultra-density optical disks, flash memory cards (e.g., SD cards, mini-SD cards, micro-SD cards, etc.), and so on. In some embodiments, image data and/or subject data can be stored in one or more remote locations, e.g., cloud storage, and synchronized with other the components of system 100. When the terms "memory" or "a memory" are used herein, they may refer to one or more memories, such as a plurality of memories.

In some embodiments, storage subsystem 104 can store one or more software programs to be executed by processing subsystem 102, such as an image visualization and analysis application 120. "Software" refers generally to sequences of instructions that, when executed by processing subsystem 102, cause system 100 to perform various operations, thus defining one or more specific machine implementations that execute and perform the operations of the software programs. Thus, "software" can also include firmware or embedded applications or any other type of instructions readable and executable by processing subsystem 102. Software can be implemented as a single program or a collection of separate programs or program modules that interact as desired. In some embodiments, programs and/or data can be stored in non-volatile storage and copied in whole or in part to volatile working memory during program execution. From storage subsystem 104, processing subsystem 102 can retrieve program instructions to execute and data to process in order to execute various operations including operations described below.

In some embodiments, the software may be run locally on system 100 but accessed and/or controlled remotely, such as through a client portal 116. For example, an instance of the image visualization and analysis application 120 may be run locally on system 100 but a remote operator may access the image visualization and analysis application 120 by means of a network connected client portal 116 such that a remote user may control the instance of the image visualization and analysis application 120 to facilitate the review, interpretation, and analysis of image data (e.g. a scanned image of a biological sample retrieved from the storage subsystem 104 and presented to the remote user for analysis).

A user interface can be provided to a display 108, and/or and one or more other user output devices (not shown). The user interface may include, for example, visualizations and other representations, the representations including images derived from scans of stained biological samples (e.g. samples stained for the presence of one or more biomarkers or stained with hematoxylin and eosin), menu bars, drop-down menus, and/or panels. The user interface provided to the display may be adapted such that only contextually relevant tools and/or viewer panels are provided to the user based on, for example, user selections including, but not limited to, a user selected zoom or magnification level. User input devices 106 can include any device via which a user can provide signals to system 100; system 100 can interpret the signals as indicative of particular user requests or information. In some embodiments, user input devices 106 can include any or all of a keyboard touch pad, touch screen (e.g., a touch-sensitive overlay on a display surface of display 108), mouse or other pointing device, scroll wheel, click wheel, dial, button, switch, keypad, microphone, and so on.

Display 108 can display visualizations (e.g. representations including image data, viewer panels to convey information to a user, or contextual menus which provide user selectable configuration options, etc.) generated by system 100 and can include various image generation technologies, e.g., a cathode ray tube (CRT), liquid crystal display (LCD), light-emitting diode (LED) including organic light-emitting diodes (OLED), projection system, or the like, together with supporting electronics (e.g., digital-to-analog or analog-to-digital converters, signal processors, or the like). Some embodiments can include a device such as a touchscreen that function as both input and output device. In some embodiments, other user output devices can be provided in addition to or instead of display 108.

In some embodiments, the user interface can provide a graphical user interface, in which visible image elements in certain areas of display 108 are defined as active elements, interactive elements, or control elements that the user selects using user input device 106. For example, the user can manipulate a user input device 106 to position an on-screen cursor or pointer over the control element, then "click" a button to indicate the selection, with the selection sending signals to perform a designated action or routine. For example, the user can manipulate the user input device 106 to select an icon within the user interface (such as one in a viewer panel, in a menu bar, or within a drop down menu), which would effectuate the initiation of an operation or selection of a tool, e.g. initiate the annotation of one or more displayed representations of an image of a tissue sample. By way of another example, the user may click on a menu bar icon to initiate the selection of a tool such that a region of interest may be selected by the user based on received inputs. In some embodiments, the user can manipulate the user input device 106 so as to interact with dropdown menus to select one or more panels, including interactive panels. In some embodiments, these selections may only be made by the user if the tools and/or viewer panels are enabled based on whether pre-established conditions are met, e.g. whether a certain zoom level is selected by a user, whether a particular tissue type is selected, whether a particular slide having a certain biomarker is selected.

Alternatively, the user can touch the control element (e.g., with a finger or stylus) on a touchscreen device. In some embodiments, the user can speak one or more words associated with the control element (the word can be, e.g., a label on the element or a function associated with the element). In some embodiments, user gestures on a touch-sensitive device can be recognized and interpreted as input commands; these gestures can be, but need not be, associated with any particular area on display 108. Other user interfaces can also be implemented.

Network interface 112 may provide data communication capability for system 100. In some embodiments, network interface 112 can include radio frequency (RF) transceiver components for accessing wireless voice and/or data networks (e.g., using cellular telephone technology, advanced data network technology such as 3G, 4G or EDGE, 5G, WiFi (IEEE 802.11 family standards), or other mobile communication technologies, or any combination thereof, GPS receiver components, and/or other components. In some embodiments, network interface 112 can provide wired network connectivity (e.g., Ethernet) in addition to or instead of a wireless interface. Network interface 112 can be implemented using a combination of hardware (e.g., antennas, modulators/demodulators, encoders/decoders, and other analog and/or digital signal processing circuits) and software components. Network interface 112 may facilitate remote access to system 100, such as through a client portal 116 (for example, a remote user may access system 100 through a remote computer and the remote computer interacts with system 100 through the network interface 112). In some embodiments, the client portal 116 is a stand-alone application that is run by a remote user on a remote computer or other computing device. In some embodiments, the client portal 116 is a web-browser running on the remote computer or other computing device which accesses system 100 through a network.

Bus 114 can include various system, peripheral, and chipset buses that communicatively connect the numerous components of system 100. For example, bus 114 can communicatively couple processing subsystem 102 with storage subsystem 104. Bus 114 can also connect to user input devices 106 and display 108. Bus 114 can also couple processing subsystem 102 to a network through network interface 112. In this manner, system 100 can be connected to a network of multiple computer systems (e.g., a local area network (LAN), a wide area network (WAN), an Intranet, or a network of networks, such as the Internet. The skilled artisan will appreciate that additional components may be connected to bus 114, such as a scanning device, a scanning device, a tissue processing system, etc.

Some embodiments include electronic components, such as microprocessors, storage and memory that store computer program instructions in a computer readable storage medium. Many of the features described herein may be implemented as processes that are specified as a set of program instructions encoded on a computer readable storage medium. When these program instructions are executed by one or more processing units, they cause the processing unit(s) to perform various operation indicated in the program instructions. Examples of program instructions or computer code include machine code, such as is produced by a compiler, and files including higher-level code that are executed by a computer, an electronic component, or a microprocessor using an interpreter.

Through suitable programming, processing subsystem 102 can provide various functionalities for system 100. For example, processing subsystem 102 can execute an image visualization and analysis application 120 having a user interface which facilitates the review and interpretation of scanned images of biological samples. The image visualization and analysis application 120 can provide various functionality such as the ability to select user configurable options or user selectable panels, or the ability to control navigation and annotate the images. In some embodiments, the analysis application 120 includes logic such that only relevant user items (informative items, user selectable items, interactive items) are presented to the user based upon whether a pre-established condition is met, e.g. whether a zoom level meeting or exceeding a predefined threshold is selected by the user or whether a certain type image is selected for review which is stained for the presence of a particular biomarker. In some embodiments, additional components may be incorporated into the system and software of the present disclosure, including those components identified in United States Patent Application Publication No. 2012/0320094, the disclosure of which is hereby incorporated by reference herein in its entirety.

In some embodiments, the image visualization and analysis application 120 incorporates various interoperating modules (e.g., blocks of code) that, when executed by one or more processors within the processing subsystem 102, implement aspects of the interface operation. For example, the image visualization and analysis application 120 can include a content fetcher 122, a content renderer 124, a GUI renderer 126, and a UI interpreter 128.

In some embodiments, content fetcher 122 can include instructions for interacting with (e.g. accessing) a local database (e.g. storage subsystem 104) or with network interface 112 to fetch or otherwise retrieve content items, such as image data and/or subject data. In some embodiments, the content fetcher 122 is configured to access a plurality of scanned images, each of the scanned images derived from a subject sample, and where each of the scanned images may each be stained for the presence of one or more biomarkers or for hematoxylin and eosin. In some embodiments, the content fetcher 122 is configured to retrieve subject information, image metadata, case history information, etc. In some embodiments, content fetcher 122 can include instructions for interacting with scanning device 110 such that image data may be acquired from one or more slides having a tissue sample stained for the presence of one or more biomarkers.

In some embodiments, content renderer 124 can include instructions for interpreting fetched content items from one or more sources and then populating or delivering the rendered content to image placeholders or other representations generated by the GUI renderer 126. For example, content renderer 124 may populate one or more rendered representations with image data retrieved from content fetcher 122 (see representation 401 of FIG. 4A). In some embodiments, the content renderer 124 can deliver subject information to other GUI elements, such as one or more viewer panels, or place the retrieved subject information into a portion of a GUI representation. In some embodiments, the content renderer 124 may deliver metadata to other GUI elements, e.g. tissue type, stains applied, scanning parameters, z-stack layers, focus layers, etc. In some embodiments, content renderer 124 can also process the acquired image data, e.g., applying any pre-processing to acquired images.

In some embodiments, GUI renderer 126 creates graphical user interface (GUI) elements to be presented to the user along with the content items rendered by content renderer 124 or other system modules. GUI renderer 126 can include code defining the location and appearance of GUI elements, such as a menu bar items and viewer panels, each of which may be interactive elements themselves or which may include interactive elements. In some embodiments, the GUI renderer 126, together with signals received from the UI interpreter 128, may determine whether certain menu bar items or viewer panels should be enabled or made otherwise available to a user, such as depending on whether a pre-established condition has been met, e.g. whether a threshold zoom level or magnification level has been selected. For example, a menu bar item may be activated by a user, whereby the user would then be allowed to select configuration options or panel views from a drop-down menu (see, e.g., FIGS. 5A and 5B). In some embodiments, the GUI renderer 126 can incorporate acquired image data provided from the content fetcher 122 or the content renderer 124 into some or all of the GUI elements (e.g. an actual image of a scanned biological sample may be displayed within a representation within the user interface, etc.).

Figure 4A:
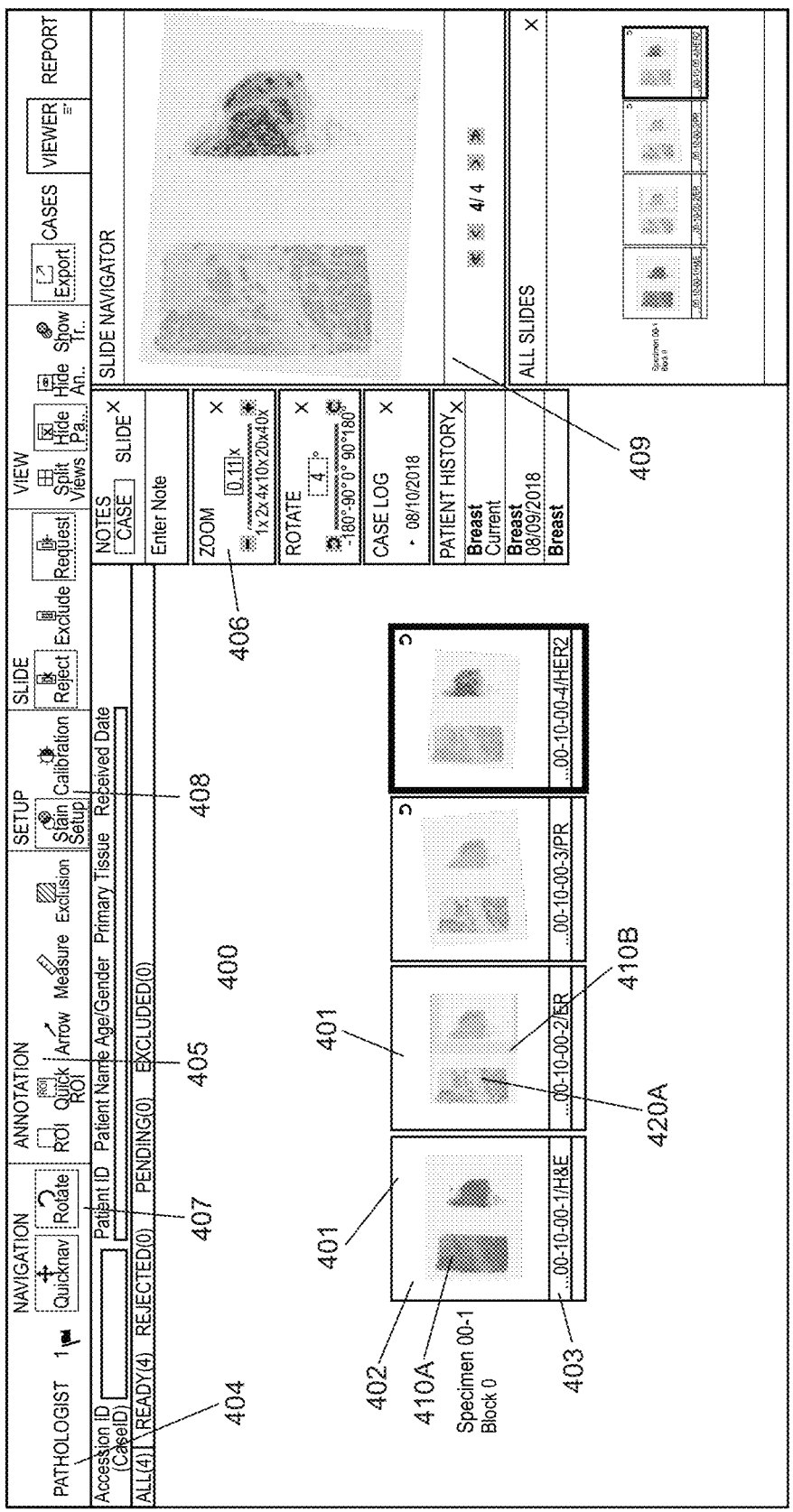
FIG. 4A illustrates a viewer window comprising a visualization including a plurality of representations at a first zoom level in accordance with some embodiments.
Figure 4B:
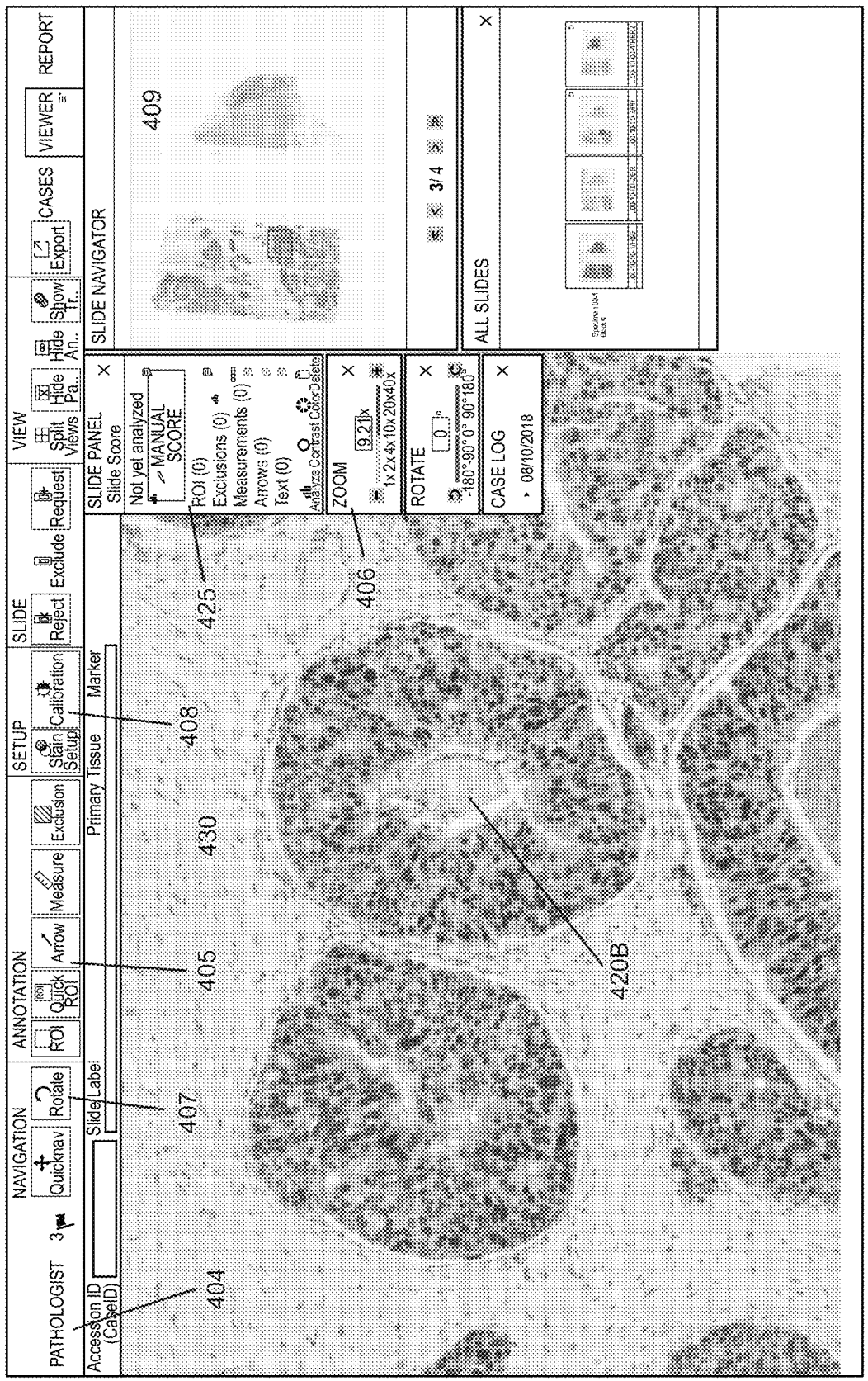
FIG. 4B illustrates a viewer window comprising a visualization including representation at a second zoom level, the second zoom level being greater than the first zoom level of FIG. 4A in accordance with some embodiments.
Figure 4C:
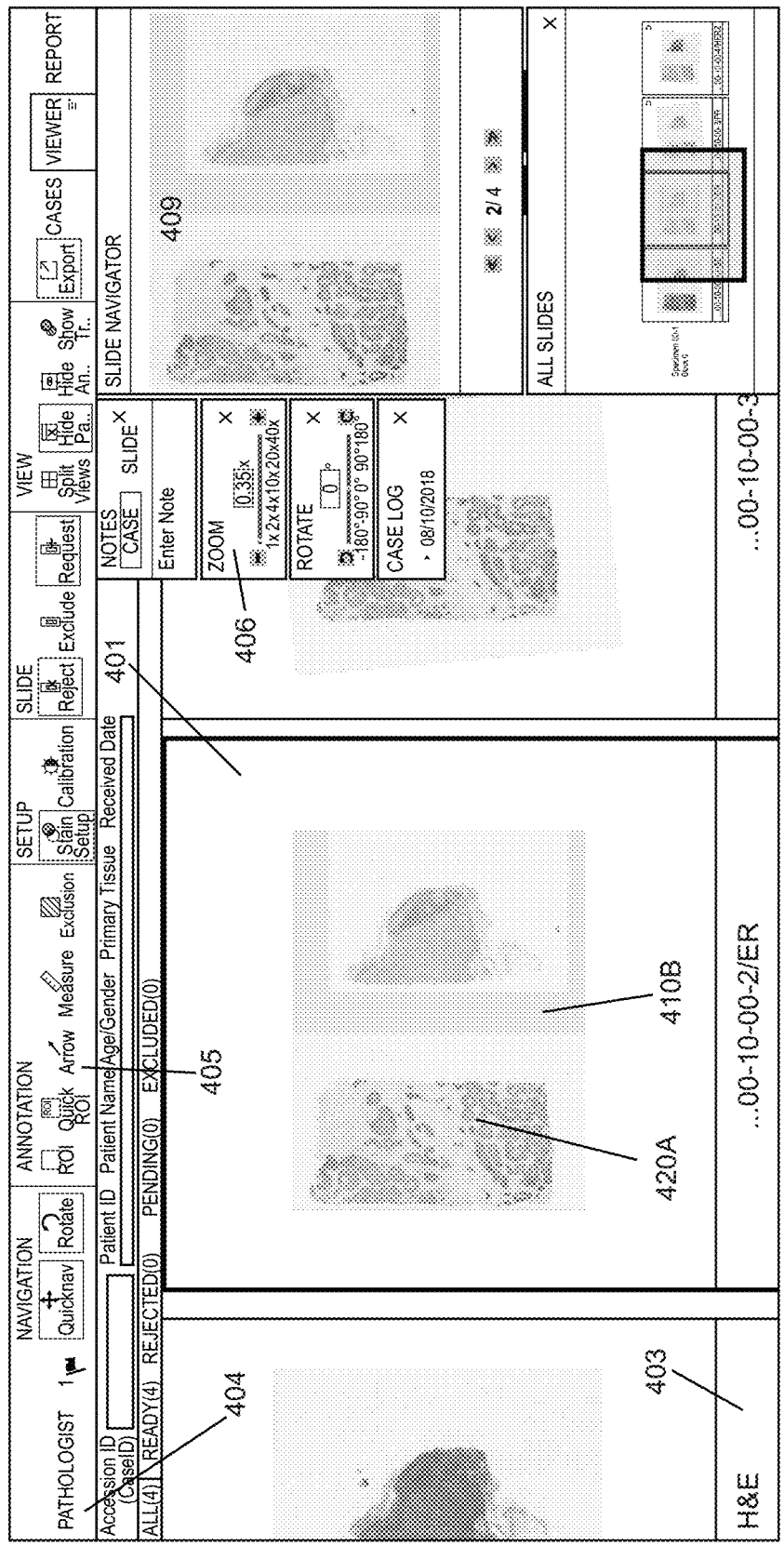
FIG. 4C illustrates a viewer window comprising a visualization including a plurality of representations at a third zoom level, the third zoom level being between the first and second zoom levels of FIGS. 4A and 4B, respectively, in accordance with some embodiments.

By way of example, the GUI renderer 126 may generate a series of representations 401 which may be populated with image data retrieved by the content fetcher 122. Examples of representations are illustrated in FIGS. 4A, 4B, and 4C. These representations may be interactive representations. For example, if a user clicks on any particular representation (e.g. representation 401 of FIG. 4A) (such as interpreted by UI interpreter 128), the GUI renderer 126 may update the corresponding display in a viewer panel, such as a slide navigator viewer panel.

Likewise, the GUI renderer 126 may generate a series of viewer panels. In some embodiments, the generated viewer panels are interactive panels where a user may select certain configurable options. For example, a zoom panel may include a slider bar where a user can select a particular preset zoom level, e.g. 1×, 2×, 10×, 40×, etc., or where the user can input a particular zoom level value. In some embodiments, the viewer panels are configured to convey relevant information to a user, e.g. a case log panel may provide a history of the user configurable selections made by the user during analysis of the image data. In addition, the GUI renderer 126 may render a visualization that shows hidden or items which are unavailable or not enabled for a user to interact with.

UI interpreter 128 can receive user input, e.g., via a user input device 106, and can interpret the input to determine actions to be performed by the analysis application 120. For example, UI interpreter 28 can determine which GUI element (e.g. an icon, or a selectable item in menu, context menu, dropdown list, buttons, a representation, etc.) the user selected and initiate the corresponding action (e.g., add an annotation, display additional content information, zoom to a selected zoom level generate a report for exporting). For example, the UI interpreter 128 may detect if a user selects an annotation tool (see annotation tools 405 in FIGS. 4A and 4B) and may send a signal to the GUI renderer 126 to display additional user selected items. In some embodiments, the annotation tools include a manual region of interest (ROI) generation tool, an automated ROI generation tool, a tool which allows the drawing of a shape (e.g. an arrow), a measurement tool, or a text input generation tool. Each of these tools may be independently disabled or hidden based on the context of user interactions. In some embodiments, menu items which may be selected include those that run certain image processing algorithms, e.g. membrane detection algorithms, cell detection and counting algorithms, nucleus detection algorithms, scoring algorithms, heat map generation algorithms, tissue masking algorithms, tissue type identification algorithms, etc. (see, for example, PCT Publication Nos. WO2016/120442 and WO2015/113895 and US Patent Application Publication Nos. 2017/0154420, 2017/0372117, 2017/0103521, 2017/0140246, 2015/0347702, 2017/0082627, 2014/0377753, 2017/0337695, 2017/0323148 and 2017/0243051, the disclosures of which are hereby incorporated by reference herein in their entireties). Inputs received from the UI interpreter 128 may be used to determine whether a pre-established condition has been met.

It will be appreciated that system 100 is illustrative and that variations and modifications are possible. Further, while system 100 is described with reference to particular blocks, it is to be understood that these blocks are defined for convenience of description and are not intended to imply a particular physical arrangement of component parts. Further, the blocks need not correspond to physically distinct components. Blocks can be configured to perform various operations, e.g., by programming a processor or providing appropriate control circuitry, and various blocks might or might not be reconfigurable depending on how the initial configuration is accessed. Embodiments of the present disclosure can be realized in a variety of apparatus including electronic devices implemented using any combination of circuitry and software. Image visualization and analysis application 120 is also illustrative, and specific implementations may include more or fewer modules than described herein. Moreover, while a particular module may be described as performing a particular function, such descriptions are not intended to imply a particular function performed by the module or a particular set of instructions included within such module.

Figure 2B:
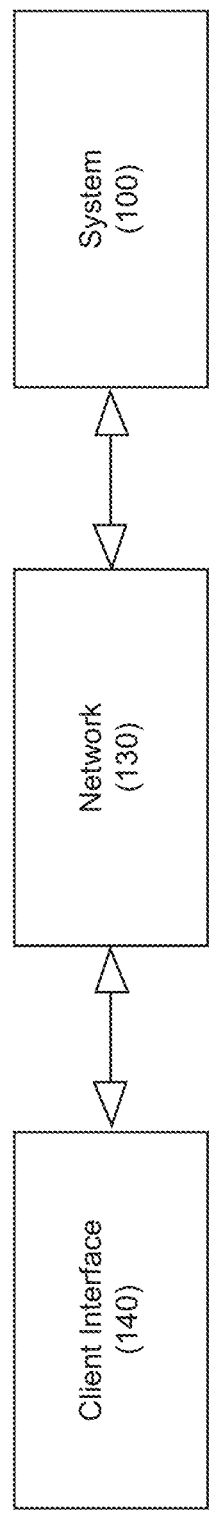
FIG. 2B sets forth a block diagram of a system communicatively coupled with a client interface through a network in accordance with some embodiments.

FIG. 2B depicts a client interface 140 in communication with a network 130 and a system 100 (such as the systems depicted in FIGS. 1 and 2). The client interface 140 may be a stand-alone application (e.g. stand-alone image visualization and analysis software) or a web-browser or other interface software which allows remote access to image visualization and analysis application 120. For example, client interface 140 allows a remote operator to log-into system 100 (such as the system depicted in FIGS. 1 and 2) and access stored image data (such as data stored in storage subsystem 104 or other network attached storage device) or image data uploaded to system 100 for processing. In some embodiments, the client interface 140 may include any of the software modules described herein. In this way, a remote user may remotely interact with elements of the system (e.g. configurable elements) such that image data may be analyzed and/or interpreted (e.g. a histologist or pathologist may select user configurable parameters, such as menu bar tools and/or viewer panels.

In some embodiments, the graphical user interface is adapted to display only certain features depending upon the zoom level selected. For example, depending on the zoom level selected, certain tools within a menu bar may not enabled (see FIG. 4A). Likewise, certain panels presented in proximity to the visualization of the accessed images may not be made available. In general, the system 100 may be configured to "restrict" access to certain tools and panels that, given a certain zoom level, would not be contextually relevant during image analysis. For example, at certain zoom levels, annotating a specific portion of an image may not be feasible if there does not exist sufficient resolution between certain features within the image. As such, if the software determines that a tool is not relevant at the select zoom level, that tool will not be enabled and, as noted above, this facilitates a quicker review of the data presented within the visualizations and also provides for an enhanced user experience and one free from potential confusion.

Figure 3:
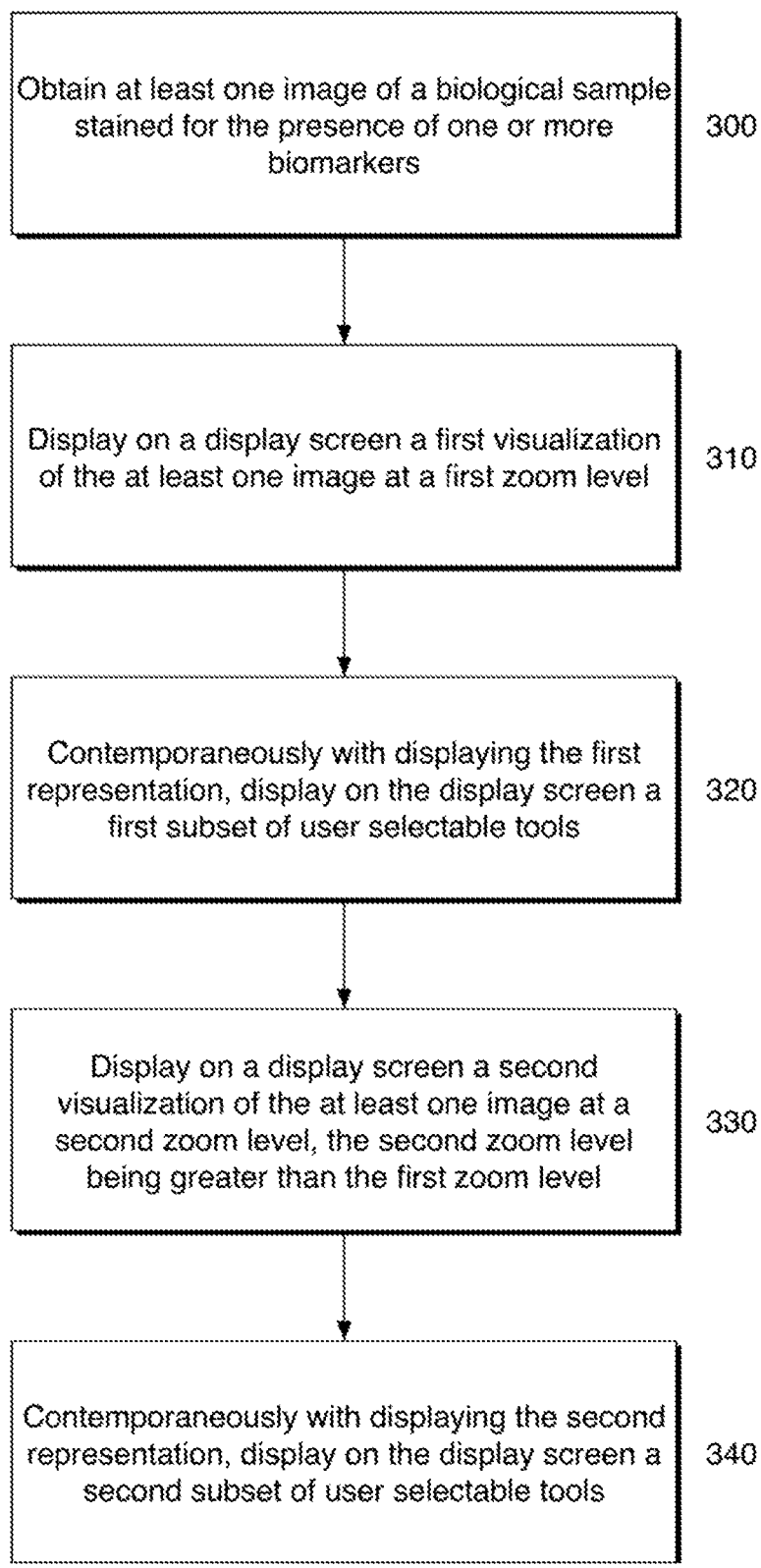
FIG. 3 sets forth a flowchart providing the general steps of displaying visualizations in accordance with some embodiments.

FIG. 3 sets forth a flowchart setting forth a method of visualizing image data associated derived from a biological sample stained for the presence of one or more biomarkers. At step 300, at least one image of a biological sample is accessed. In some embodiments, the biological sample is stained for the presence of one or more biomarkers. In some embodiments, multiple images are retrieved, such as multiple images from the same biological sample, but where each image comprises stained denoting the presence or absence of a particular biomarker.

Subsequently, a first visualization is rendered within the graphical user interface (step 310), wherein the first visualization at least includes a rendering of the at least one image at a first zoom level. In some embodiments, the first visualization 400 includes a rendering of multiple accessed images (see, e.g., FIG. 4A). In some embodiments, the first visualization includes a series of representations 401 (e.g. image placeholders) where each representation 401 may include one of the accessed images 410A or 410B. In some embodiments, each representation 401 is the same size and/or shape. In some embodiments, each representation 401 comprises a first portion 402 which includes one of the accessed images 410 and a second portion 403 which includes identifying indicia. In some embodiments, the identifying indicia includes an identification of the stain appearing in the image or the biomarker which was stained.

By way of example, a second portion 403 of representation 401 indicates that the particular image 410A within the first portion 402 was stained with hematoxylin and eosin.

In some embodiments, a first series of tools (e.g. annotation tools 405) within a menu bar 404 are contemporaneously displayed with the first visualization 400 (step 320). As noted above, and as illustrated in FIG. 4A, some of the tools are unavailable for selection, i.e. they are "greyed out" (see, e.g., setup calibration tool 408) while other tools are available for selection and appearing as white icons (see, e.g., rotation tool 407). By way of further example, each of the five annotation tools 405 are greyed out and thus disabled. In some embodiments, certain tools may be completely hidden from a user at a particular zoom level as described further herein. As such, the first series of tools (i.e. those available for selection and/or represented as white icons) represents a subset of all of those tools that may be available to the user. Given the zoom level of the four images depicted in the representations 401 of FIG. 4A, it is believed that those tools which are not available, i.e. those that are "greyed out," would not be relevant at the given zoom level of 1× as illustrated in FIG. 4A. Said another way, those tools that are not enabled or which are hidden from user selection are determined to be ineffective at the selected zoom level. For example, it is believed that there would be no value for the histologist or pathologist to perform a measurement or to draw an arrow to a cell since, at the given zoom level (e.g. 1×), sufficient cellular features would not be able to be resolved such that a measurement could accurately be made or that an arrow could correctly be placed pointing to a particular desired structure.

Figure 5A:
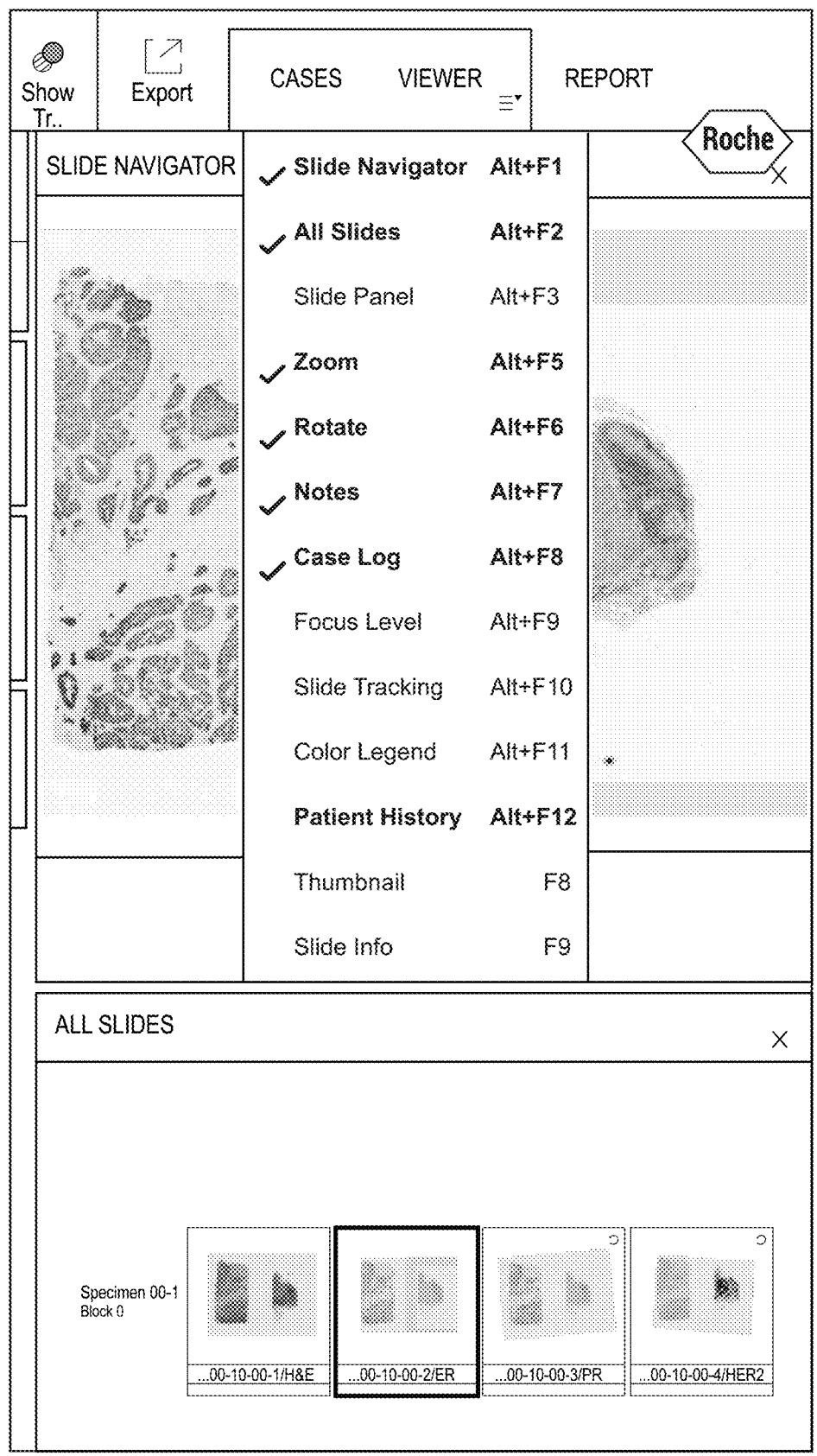
FIG. 5A illustrates a dropdown menu for the selection of certain viewer panels, such as those available at a first zoom level (e.g. the zoom level in FIG. 4A), in accordance with some embodiments.
Figure 5B:
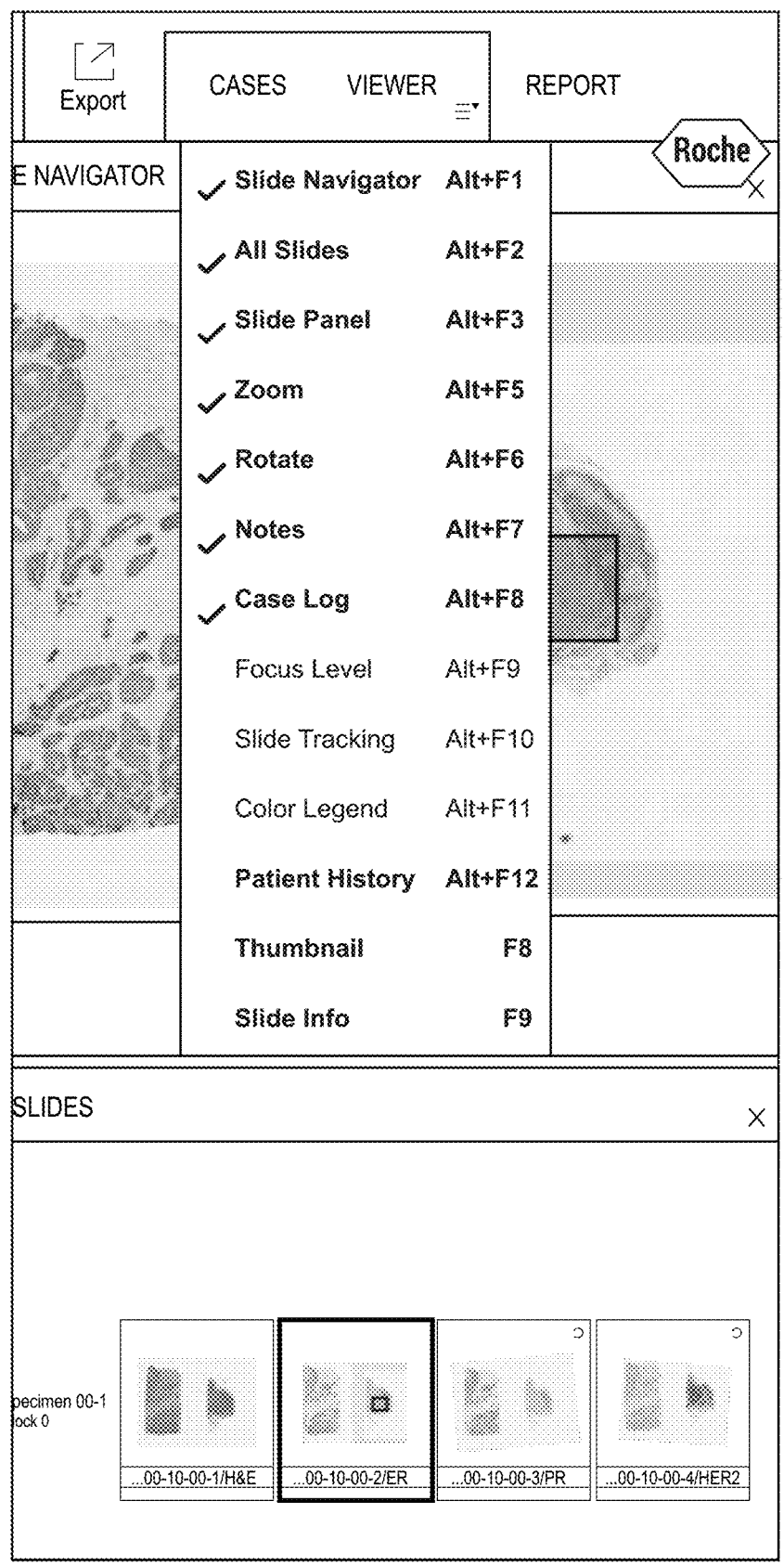
FIG. 5B illustrates a dropdown menu for the selection of certain viewer panels, such as those available at a second zoom level (e.g. the zoom level in FIG. 4B), in accordance with some embodiments.

In some embodiments, a first set of panels may also be contemporaneously displayed with the first visualization and with the first series of tools. For example, a zoom panel 406 and a slide navigator panel 409 may contemporaneously be displayed with the first visualization and with the first series of tools. As with the first series of tools, only those panels that are contextually relevant at the given level of zoom are presented. For example, FIG. 5A illustrates panels that may be selected by a user in a contextual or dropdown menu. Those items that are not available are not able to be selected and are "greyed out." Likewise, those panels that are able to be selected are shown in white and are able to be selected by the user. Moreover, those panels that have already been selected may be marked with an indicia, e.g. a check mark.

Following the contemporaneous presentation of the first visualization (e.g. the three representations 401 in FIG. 4A) and of the first series of tools (those that are not "greyed out" in menu bar 404), and/or the first set of panels, a user may then interact with the visualization such as to change the zoom level, e.g. to increase the zoom of one or more of the accessed images presented in the first visualization, enabling the user to view at least a portion of one of the accessed images in greater detail, and thereby providing at least a second visualization at a second zoom level 430. By "increasing the zoom" or "zooming into the image" it is meant that a portion of the image is magnified thereby increasing the visual resolution of that portion of the image. For example, accessed image 410B is presented in FIG. 4A at a 1× zoom level, and it will be appreciated that at this zoom level certain tissue structures, e.g. 420A, are difficult to decipher. When, however, the zoom level of image 410B is increased as shown in FIG. 4B (e.g. increasing the zoom level from 1× to about 10×), the magnification and/or resolution of the tissue structure 420B is shown in greater detail, e.g. at a level where individual cells may be resolved.

Contemporaneous with the display of the second visualization (step 330) at the second zoom level 430, a second series of tools in a menu bar 404 are displayed (step 340). Like the first series of tools, the second series of tools again represents a subset of all of those tools available to a user. By way of example, and in comparison, to the first series of tools available (see FIG. 4A), the second series of tools includes each of the five annotation tools 405 (see FIG. 4B).

In the particular embodiment illustrated in FIG. 4B, the second set of tools is inclusive of the first series of tools, i.e. the second set of tools includes all of those tools available in the first series. In some embodiments, the second set of tools does not include all of the tools provided in the first series. In some embodiments, the second series of tools comprises at least one different tool than that provided in the first series of tools.

In some embodiments, a second set of panels are displayed contemporaneously with the second visualization at the second zoom level 430 and with the second series of tools. As with the second series of tools, only those panels that are contextually relevant at the given level of zoom are presented. In the embodiment illustrated in FIG. 4B, and as compared with the embodiment of FIG. 4A, a slide panel 425 is automatically displayed at the about 10× zoom level. Turning to FIG. 5B, once again those items that are not available are not able to be selected and are "greyed out." Likewise, those viewer panels that are able to be selected are shown in white and are able to be selected by the user. Moreover, those panels that have already been selected are marked with an indicia, e.g. a check mark.

FIG. 4C illustrates the selection of a zoom level (e.g. an intermediate zoom level) that falls between the zoom level depicted in FIG. 4A and the zoom level depicted in FIG. 4B. While four representations 401 were illustrated in FIG. 4A at a zoom level of 1×, at the zoom level in FIG. 4C, only three representations are visualized, and only one of the three representations is fully visualized. Notably, the same tools appear as available in FIG. 4C as in FIG. 4A. Likewise, the same panels appear in FIG. 4C as in FIG. 4A. As such, FIG. 4C illustrates that a threshold zoom value has not been reached by the user such that the image visualization and analysis application 420 would make available other tools in menu bar 404 or, for that matter, make available other viewer panels available. In this regard, FIG. 4C illustrates that items displayed and made available to a user are contextually dependent, here contextually dependent upon the level of zoom selected by a user.

In some embodiments, each of the menu items and/or viewer panels have a pre-programmed threshold zoom level that must be attained prior to enabling the respective menu items and/or viewer panels available. For example, with reference to FIG. 4A, the annotation tools 405 may only become available when a user selects a zoom level which exceeds a pre-determined threshold zoom level value, e.g. 5×. In some embodiments, each individual tool within the menu bar 404 may have a different pre-determined threshold value. For example, a first annotation tool may have a predetermined threshold value of 2×, a second annotation tool may have a predetermined threshold value of 6×, and a slide calibration tool may have a predetermined threshold value of 10×. In some embodiments, the threshold zoom value may depend on a tissue type or a stain being observed.

In some embodiments, the threshold for whether to make available a menu bar items or a viewer panel does not need to be tied to a predetermined threshold zoom value, i.e. a value of 1×, 2×, 4×, 8×, 16×, 32×, etc. Rather, the threshold can be tied to whether a zoom level is selected where individual cells or individual nuclei may be resolved by a user. Alternatively, the threshold can be tied to whether a zoom level is selected where a certain number of cells are present a predefined area (pixel×pixel), e.g. 100 cells in a 500 pixel×500 pixel area. In some embodiments, different elements may be visualized depending on the available display resolution. For example, the threshold may be predefined as "p" if a display resolution is "m×n," but may be predefined as "p*q" if the display resolution is (m*q×n*q), where q is a scaling factor to account for differences in display resolutions. In yet other embodiments, whether certain viewer panels may be displayed or hidden may be tied to an available display resolution. For example, although 5 viewer panels may be made available or unhidden when a threshold zoom level is reached (i.e. they become contextually relevant and made available), the system may continue to hide certain panels if available screen "real estate" is not available due to low or limited display resolution, and the system may determine which of the available viewer panels are most relevant given the display resolution limitations and prioritize those panels for display. In addition, and by way of example, the viewer panels could be cycled as needed to accommodate for limited display resolutions.

Figure 6A:
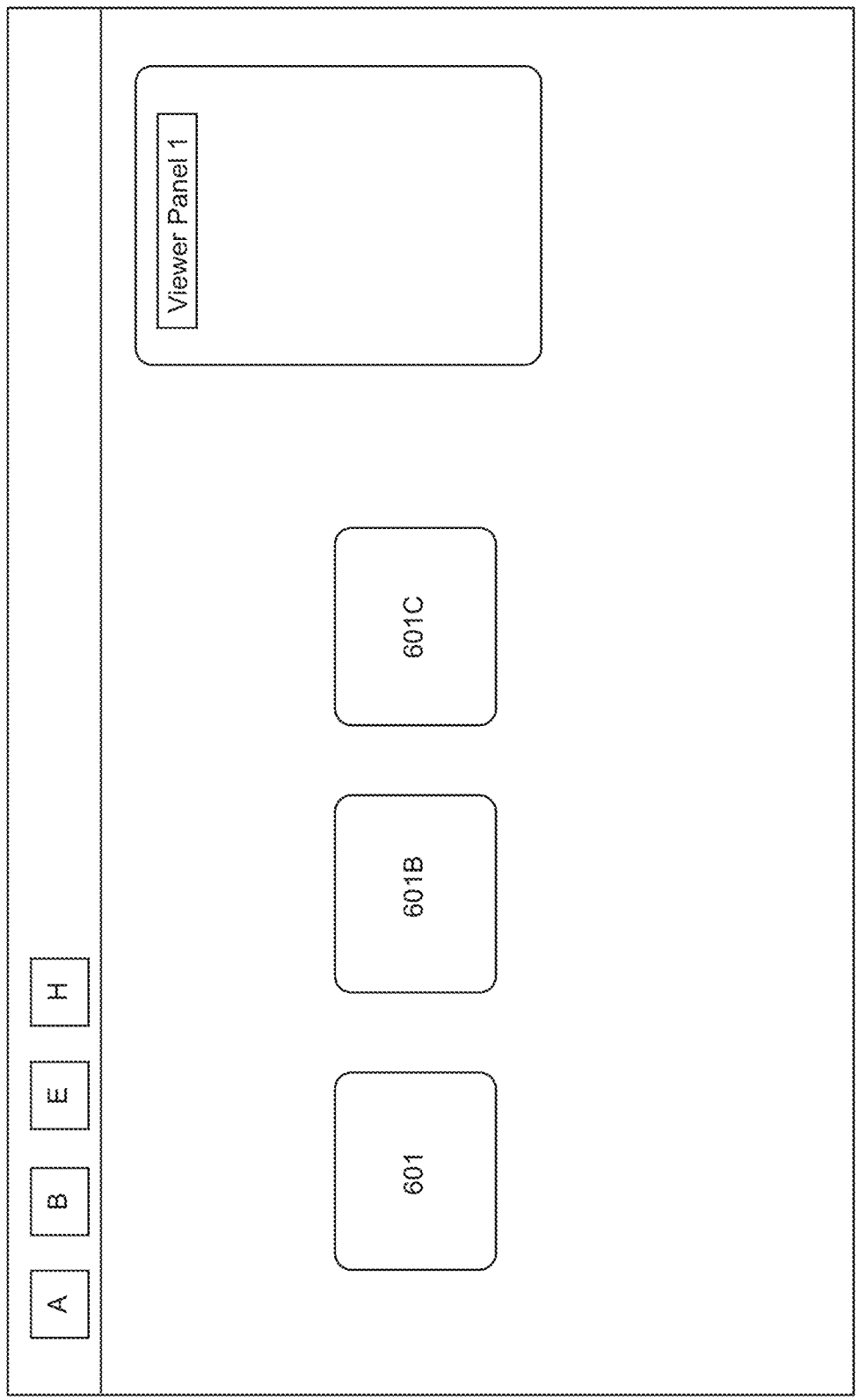
FIG. 6A illustrates a viewer window comprising a first visualization including three representations at a first zoom level, in accordance with some embodiments.
Figure 6B:
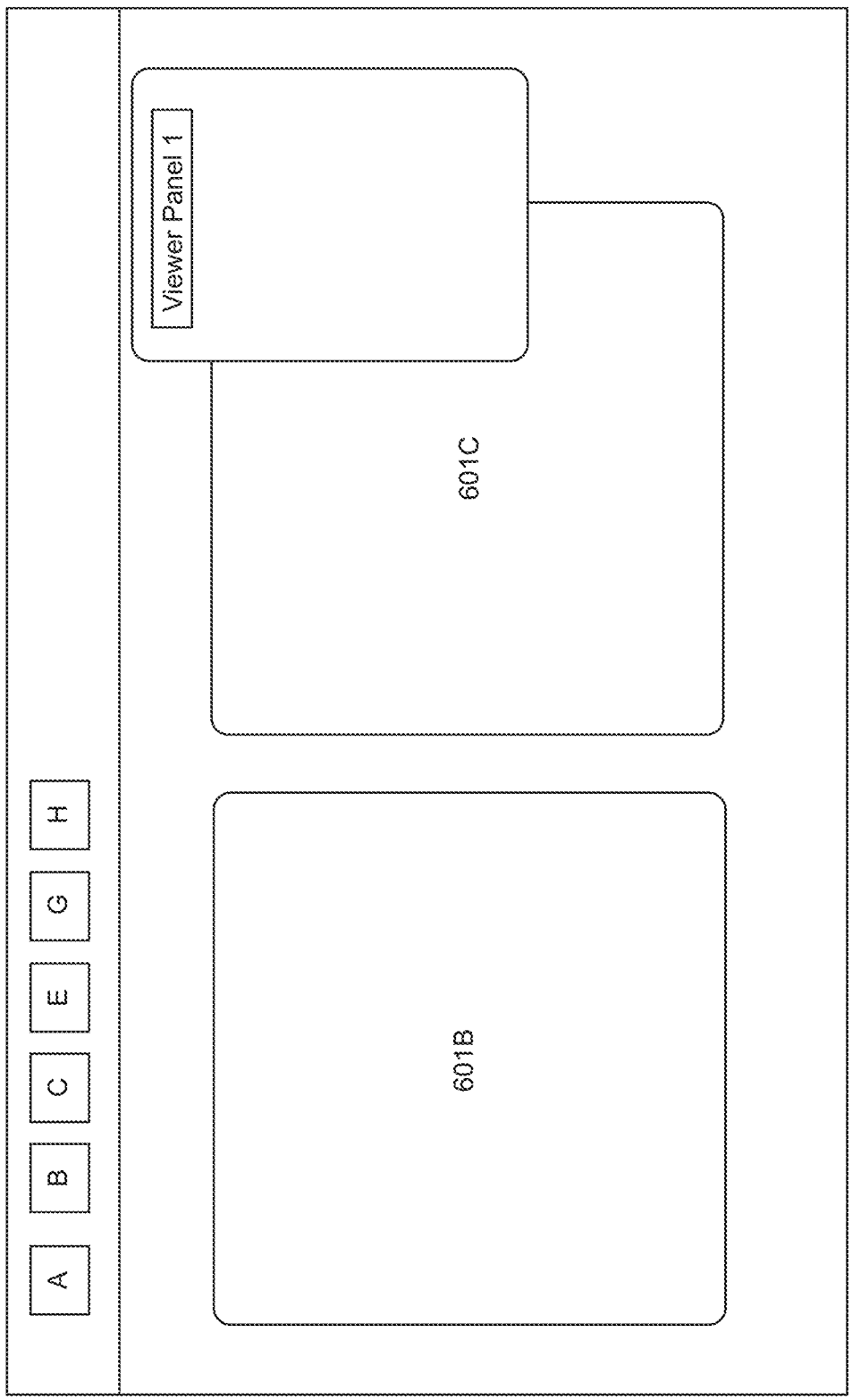
FIG. 6B illustrates a viewer window comprising a first visualization including three representations at a second zoom level, an intermediate zoom level as compared with zoom levels depicted in FIGS. 6A and 6C, in accordance with some embodiments.
Figure 6C:
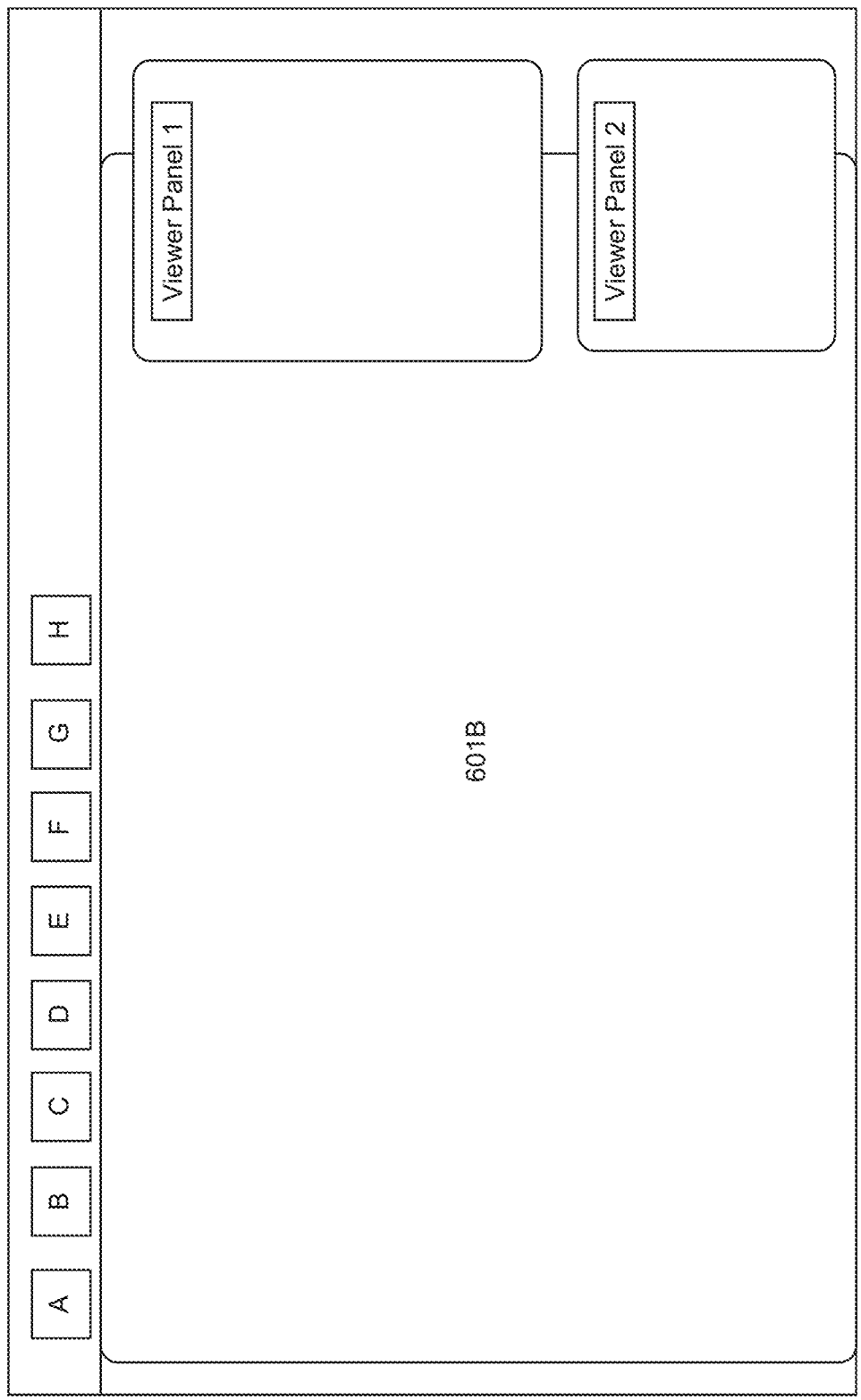
FIG. 6C illustrates a viewer window comprising a first visualization including three representations at a third zoom level, the third zoom level being greater than the zoom level in FIGS. 6A and 6B, in accordance with some embodiments.

As noted herein, in some embodiments, entire menu items may be hidden until a particular zoom level is selected by the user. For example, assume that a menu bar were to include items A, B, C, D, E, F, G, and H. Further assume, that a zoom level of 1×, that only menu bar items A, B, E, and H are shown within a graphical user interface, as depicted in FIG. 6A. According to the present disclosure, those menu bar items A, B, E, and H are the only tools relevant and useful for a user at a zoom level of 1×. Once the user zooms into one of the images (see FIG. 6B), additional menu bar items may be shown, e.g. menu bar items C and G, provided that menu bar items (i.e. C and G) are relevant to the level of zoom selected (e.g. 3×). Once the user further zooms into one of the images (see FIG. 6C), here 601B, yet additional menu bar items may be shown, i.e. D and F, again provided that those yet additional menu bar items are relevant at the level of zoom selected (e.g. 8×). FIG. 6C further illustrates that a second viewer panel, i.e. "Viewer Panel 2," becomes shown by the graphical user interface, but again only when a particular zoom level is reached (i.e. at least a zoom level greater than 3×, such as at 8×).

In some embodiments, an input image is received by the visualization system and visualizations are provided at a default zoom level, e.g. a zoom level of 1×. In some embodiments, the system receives a user input, e.g. a selection of an updated zoom level, a selection of a particular image. In some embodiments, a comparison is made between the received user input and threshold conditions, e.g. a comparison is made between a received user input of a zoom level to determine if a threshold zoom level is attained or a comparison is made between a received user input of an image selection to determine the biomarkers identified in the image. In some embodiments, if a threshold zoom level is met, then additional visualization elements (e.g. tools, panels) may be presented to the user. In some embodiments, if different biomarkers are selected in a second image as compared with a first image, then additional visualization elements may be presented to the user. In some embodiments, at least one GUI element is changed based on a user selection.

Additional Embodiments

In some embodiments, each displayed visualization or element has a position within a coordinate system of a display provided within an interface application, such as a browser. For example, icons for tools, such as image analysis tools, have a position within a display coordinate system. For instance, if a display has a resolution of 4,000×3000 and each pixel is considered a point in a coordinate system, then an icon for an annotation tool may have a position defined by an area of pixels [150, 200] (top left corner), [160, 200] (top right corner), [150, 210] (bottom left corner), and [160, 210] (bottom right corner). In some embodiments, viewer panels, image data, and other representations may have positions within the coordinate system of the display. In some embodiments, a first viewer panel may have a first positional area while a second viewer element may have a second position area. In some embodiments, each viewer panel may have a variable positional area depending on the type of information being displayed and the quantity of information available. In some embodiments, the positions of various elements within the coordinate system of the display may be fixed or may be variable depending upon context.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus. Any of the modules described herein may include logic that is executed by the processor(s). "Logic," as used herein, refers to any information having the form of instruction signals and/or data that may be applied to affect the operation of a processor. Software is an example of logic.

A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or can be included in, one or more separate physical components or media (e.g., multiple CDs, disks, or other storage devices). The operations described in this specification can be implemented as operations performed by a data processing apparatus on data stored on one or more computer-readable storage devices or received from other sources.

The term "programmed processor" encompasses all kinds of apparatus, devices, and machines for processing data, including by way of example a programmable microprocessor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus also can include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random-access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., an LCD (liquid crystal display), LED (light emitting diode) display, or OLED (organic light emitting diode) display, for displaying information to the user and a keyboard and a pointing device, e.g., a mouse or a trackball, by which the user can provide input to the computer. In some implementations, a touch screen can be used to display information and receive input from a user. Other kinds of devices can be used to provide for interaction with a user as well; for example, feedback provided to the user can be in any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks). For example, the network 20 of FIG. 1 can include one or more local area networks.

The computing system can include any number of clients and servers. A client and server are generally remote from each other and typically interact through a communication network. The relationship of client and server arises by virtue of computer programs running on the respective computers and having a client-server relationship to each other. In some embodiments, a server transmits data (e.g., an HTML page) to a client device (e.g., for purposes of displaying data to and receiving user input from a user interacting with the client device). Data generated at the client device (e.g., a result of the user interaction) can be received from the client device at the server.

All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of some embodiments can be modified, if necessary to employ concepts of the various patents, applications and publications to provide yet further embodiments.

Although the present disclosure has been described with reference to a number of illustrative embodiments, it should be understood that numerous other modifications and embodiments can be devised by those skilled in the art that will fall within the spirit and scope of the principles of this disclosure. More particularly, reasonable variations and modifications are possible in the component parts and/or arrangements of the subject combination arrangement within the scope of the foregoing disclosure, the drawings, and the appended claims without departing from the spirit of the disclosure. In addition to variations and modifications in the component parts and/or arrangements, alternative uses will also be apparent to those skilled in the art.

The invention claimed is:

1. A computing device comprising a display screen, the computing device configured to:
    access at least one image of a biological sample stained for presence of one or more biomarkers from one or more memories communicatively coupled to the computing device, wherein the biological sample comprises a plurality of cells;

display, on the display screen, the at least one image at a first magnification level, a menu bar, and a panel area;
determine a display resolution for resolving the plurality of cells or a number of cells of the plurality of cells within a predefined area at the first magnification level;
determine the display resolution or the number of cells does not exceed a predetermined threshold value;
in response to determining the display resolution or the number of cells does not exceed the predetermined threshold value, display a plurality of first tools in the menu bar, the plurality of first tools including tools for performing one or more first operations on the at least one image displayed at the first magnification level;
receive, in the panel area, a user input to change a zoom level of the at least one image;
in response to receiving the user input to change the zoom level of the at least one image, display, on the display screen, the at least one image at a second magnification level, different than the first magnification level, the menu bar, and the panel area;
determine the display resolution for resolving the plurality of cells or the number of cells of the plurality of cells within the predefined area at the second magnification level;
determine the display resolution or the number of cells exceeds the predetermined threshold value; and
in response to determining the display resolution or the number of cells exceeds the predetermined threshold value, display a plurality of second tools in the menu bar, the plurality of second tools including tools for performing one or more second operations, different than the one or more first operations, on the at least one image displayed at the second magnification level,
wherein (i) one or more tools of the plurality of first tools displayed when the at least one image is displayed at the first magnification level are disabled or hidden when the at least one image is displayed at the second magnification level, and (ii) one or more tools of the plurality of second tools displayed when the at least one image is displayed at the second magnification level are disabled or hidden when the at least one image is displayed at the first magnification level.

2. The computing device of claim 1, wherein the second magnification level meets at least a predetermined magnification level.

3. The computing device of claim 1, wherein the one or more tools of the plurality of second tools disabled or hidden when the at least one image is displayed at the first magnification level are contextually relevant at the second magnification level, but not contextually relevant at the first magnification level.

4. The computing device of claim 1, wherein the one or more tools of the plurality of second tools comprises one or more image annotation tools.

5. The computing device of claim 4, wherein the one or more image annotation tools comprises region of interest identification tools, measurement tools, indicia drawing tools, and region exclusion tools.

6. The computing device of claim 1, wherein the one or more tools of the plurality of second tools comprises one or more image processing tools.

7. The computing device of claim 1, wherein the second magnification level is greater than the first magnification level.

8. The computing device of claim 1, wherein the panel area comprises one or more viewer panels, wherein at least one viewer panel of the one or more viewer panels is displayed when the at least one image is displayed at the second magnification level and is disabled or hidden when the at least one image is displayed at the first magnification level.

9. The computing device of claim 1, wherein the first magnification level is an unmagnified zoom level.

10. The computing device of claim 9, wherein the at least one image further comprises a portion comprising identifying indicia.

11. A computing device comprising a display screen, the computing device configured to:
access at least one image of a biological sample stained for presence of one or more biomarkers from one or more memories communicatively coupled to the computing device, wherein the biological sample comprises a plurality of cells;
display, on the display screen, the at least one image at a first magnification level, a menu bar, and a panel area;
determine a display resolution for resolving the plurality of cells or a number of cells of the plurality of cells within a predefined area at the first magnification level;
determine the display resolution or the number of cells does not exceed a predetermined threshold value;
in response to determining the display resolution or the number of cells does not exceed the predetermined threshold value, display:
a plurality of first tools in the menu bar, the plurality of first tools including tools for performing one or more first operations on the at least one image displayed at the first magnification level; and
a plurality of first panels in the panel area, the plurality of first panels including a zoom panel for magnifying the at least one image and a rotation panel for rotating the at least one image;
receive, in the zoom panel, a user input to change a zoom level of the at least one image;
in response to receiving the user input to change a zoom level of the at least one image, display, on the display screen, the at least one image at a second magnification level, different from the first magnification level, the menu bar, and the panel area;
determine the display resolution for resolving the plurality of cells or the number of cells of the plurality of cells within the predefined area at the second magnification level;
determine the display resolution or the number of cells exceeds the predetermined threshold value; and
in response to determining the display resolution or the number of cells does not exceed the predetermined threshold value, display:
a plurality of second tools in the menu bar, the plurality of second tools including tools for performing one or more second operations, different than the one or more first operations, on the at least one image displayed at the second magnification level; and
a plurality of second panels in the panel area, the plurality of second panels including the zoom panel and a slide panel for assigning a score,
wherein (i) one or more tools of the plurality of first tools displayed when the at least one image is displayed at the first magnification level are disabled or hidden when the at least one image is displayed at the second magnification level, and (ii) one or more tools of the plurality of second tools displayed when the at least one image is displayed at the second magnification level are disabled or hidden when the at least one image is displayed at the first magnification level.

12. The computing device of claim 11, wherein at least one panel of the plurality of first panels is displayed when the at least one image is displayed at the first magnification level and is disabled or hidden when the at least one image is displayed at the second magnification level.

13. The computing device of claim 11, wherein the one or more tools of the plurality of second tools comprises one or more image annotation tools, the one or more image annotation tools comprises region of interest identification tools, measurement tools, indicia drawing tools, and region exclusion tools.

14. The computing device of claim 11, wherein the first magnification level is an unmagnified zoom level and the second magnification level is greater than the first magnification level.

15. The computing device of claim 11, wherein the at least one image comprises:
(i) a first portion comprising a representation of the biological sample at the first magnification level, and
(ii) a second portion comprising identifying indicia.

16. The computing device of claim 15, wherein the identifying indicia comprises an identification of a biomarker.

17. A method comprising:
accessing at least one image of a biological sample stained for presence of one or more biomarkers from one or more memories communicatively coupled to a computing device, wherein the biological sample comprises a plurality of cells;
displaying, on a display screen, the at least one image at a first magnification level, a menu bar, and a panel area;
determining a display resolution for resolving the plurality of cells or a number of cells of the plurality of cells within a predefined area at the first magnification level;
determining the display resolution or the number of cells does not exceed a predetermined threshold value;
in response to determining the display resolution or the number of cells does not exceed the predetermined threshold value, displaying:
a plurality of first tools in the menu bar, the plurality of first tools including tools for performing one or more first operations on the at least one image displayed at the first magnification level; and
a plurality of first panels in the panel area, the plurality of first panels including a zoom panel for magnifying the at least one image and a rotation panel for rotating the at least one image;
receiving, in the zoom panel, a user input to change a zoom level of the at least one image;
in response to receiving the user input to change a zoom level of the at least one image, displaying, on the display screen, the at least one image at a second magnification level, different from the first magnification level, the menu bar, and the panel area;
determining the display resolution for resolving the plurality of cells or the number of cells of the plurality of cells within the predefined area at the second magnification level;
determining the display resolution or the number of cells exceeds the predetermined threshold hold value; and
in response to determining the display resolution or the number of cells exceeds the predetermined threshold value, displaying:
a plurality of second tools in the menu bar, the plurality of second tools including tools for performing one or more second operations, different than the one or more first operations, on the at least one image displayed at the second magnification level; and
a plurality of second panels in the panel area, the plurality of second panels including the zoom panel and a slide panel for assigning a score,
wherein (i) one or more tools of the plurality of first tools displayed when the at least one image is displayed at the first magnification level are disabled or hidden when the at least one image is displayed at the second magnification level, and (ii) one or more tools of the plurality of second tools displayed when the at least one image is displayed at the second magnification level are disabled or hidden when the at least one image is displayed at the first magnification level.

18. The method of claim 17, wherein at least one panel of the plurality of first panels is displayed when the at least one image is displayed at the first magnification level and is disabled or hidden when the at least one image is displayed at the second magnification level.

19. The method of claim 17, wherein the first magnification level is an unmagnified zoom level and the second magnification level is greater than the first magnification level.

20. The method of claim 17, wherein the at least one image comprises:
(i) a first portion comprising a representation of the biological sample at the first magnification level, and
(ii) a second portion comprising identifying indicia, wherein the identifying indicia comprises an identification of a biomarker.

21. A non-transitory computer-readable medium storing instructions which, when executed by one or more processors of a computing device, causes the computing device to:
access at least one image of a biological sample stained for presence of one or more biomarkers from one or more memories communicatively coupled to the computing device, wherein the biological sample comprises a plurality of cells;
display, on a display screen, the at least one image at a first magnification level, a menu bar, and a panel area;
determine a display resolution for resolving the plurality of cells or a number of cells of the plurality of cells within a predefined area at the first magnification level;
determine the display resolution or the number of cells does not exceed a predetermined threshold value;
in response to determining the display resolution or the number of cells does not exceed the predetermined threshold value, display:
a plurality of first tools in the menu bar, the plurality of first tools including tools for performing one or more first operations on the at least one image displayed at the first magnification level; and
a plurality of first panels in the panel area, the plurality of first panels including a zoom panel for magnifying the at least one image and a rotation panel for rotating the at least one image;
receive, in the zoom panel, a user input to change a zoom level of the at least one image;
in response to receiving the user input to change a zoom level of the at least one image, display, on the display screen, the at least one image at a second magnification level, different from the first magnification level, the menu bar, and the panel area;
determine the display resolution for resolving the plurality of cells or the number of cells of the plurality of cells within the predefined area at the second magnification level;

determine the display resolution or the number of cells exceeds the predetermined threshold value; and in response to determining the display resolution or the number of cells does not exceed the predetermined threshold value, display:
- a plurality of second tools in the menu bar, the plurality of second tools including tools for performing one or more second operations, different than the one or more first operations, on the at least one image displayed at the second magnification level; and
- a plurality of second panels in the panel area, the plurality of second panels including the zoom panel and a slide panel for assigning a score, wherein (i) one or more tools of the plurality of first tools displayed when the at least one image is displayed at the first magnification level are disabled or hidden when the at least one image is displayed at the second magnification level, and (ii) one or more tools of the plurality of second tools displayed when the at least one image is displayed at the second magnification level are disabled or hidden when the at least one image is displayed at the first magnification level.

* * * * *